United States Patent
Patane

(10) Patent No.: US 9,409,901 B2
(45) Date of Patent: Aug. 9, 2016

(54) COMPOSITIONS AND METHODS FOR TREATING OR PREVENTING DISEASES OR DISORDERS ASSOCIATED WITH MISREGULATED EIF4E

(71) Applicant: Bantam Pharmaceutical, LLC, New York, NY (US)

(72) Inventor: Michael Patane, Andover, MA (US)

(73) Assignee: Bantam Pharmaceutical, LLC, New York, NY (US)

( * ) Notice: Subject to any disclaimer, the term of this patent is extended or adjusted under 35 U.S.C. 154(b) by 0 days.

(21) Appl. No.: 14/437,251

(22) PCT Filed: Oct. 22, 2013

(86) PCT No.: PCT/US2013/066041
§ 371 (c)(1),
(2) Date: Apr. 21, 2015

(87) PCT Pub. No.: WO2014/066304
PCT Pub. Date: May 1, 2014

(65) Prior Publication Data
US 2015/0274717 A1    Oct. 1, 2015

Related U.S. Application Data

(60) Provisional application No. 61/716,987, filed on Oct. 22, 2012, provisional application No. 61/735,458, filed on Dec. 10, 2012.

(51) Int. Cl.
*C07D 417/04* (2006.01)
*C07D 417/14* (2006.01)
*A61K 45/06* (2006.01)

(52) U.S. Cl.
CPC .............. *C07D 417/14* (2013.01); *A61K 45/06* (2013.01); *C07D 417/04* (2013.01)

(58) Field of Classification Search
None
See application file for complete search history.

(56) References Cited

FOREIGN PATENT DOCUMENTS

| WO | 2008-006790 A1 | 1/2008 |
|---|---|---|
| WO | 2008-006793 A1 | 1/2008 |
| WO | 2008-054749 A1 | 5/2008 |
| WO | 2009-017701 A1 | 2/2009 |
| WO | 2012-006068 A2 | 1/2012 |

*Primary Examiner* — Laura L. Stockton
(74) *Attorney, Agent, or Firm* — McDonnell Boehnen Hulbert & Berghoff LLP

(57) ABSTRACT

Disclosed herein are compounds, compositions, formulations, kits and methods of treatment useful for treating or preventing one or more hyperproliferative disorders, e.g., cancer or a neurological disease or disorder.

22 Claims, 23 Drawing Sheets

COMPOSITIONS AND METHODS FOR TREATING OR PREVENTING DISEASES OR DISORDERS ASSOCIATED WITH MISREGULATED EIF4E

CROSS-REFERENCE TO RELATED APPLICATIONS

This application is a U.S. national phase application of International Patent Application no. PCT/US2013/066041 filed on Oct. 22, 2013, which claims the benefit of U.S. Provisional Patent Application Ser. No. 61/716,987, filed Oct. 22, 2012 and U.S. Provisional Patent Application Ser. No. 61/735,458, filed Dec. 10, 2012.

BACKGROUND

Initiation of translation usually involves the interaction of certain key proteins with a special tag bound to the 5'-end of an mRNA molecule, the 5' cap. Protein factors bind the small ribosomal subunit (also referred to as the 40 S subunit), and these "initiation factors" hold the mRNA in place. The eukaryotic Initiation Factor 3 (eIF3) is associated with the small ribosomal subunit, and plays a role in keeping the large ribosomal subunit from prematurely binding. eIF3 also interacts with the eIF4F complex which consists of three other initiation factors: eIF4A, eIF4E and eIF4G. eIF4G is a scaffolding protein that directly associates with both eIF3 and the other two components. eIF4E is the cap-binding protein. It is the rate-limiting step of CAP-dependent initiation, and is often cleaved from the complex by viral proteases to limit the cell's ability to translate its own transcripts. This is a method of hijacking the host machinery in favor of the viral (cap-independent) messages.

SUMMARY

Reproducing cells require CAP-dependent translation initiation of proteins required for cellular proliferation. In situations characterized by aberrant cellular proliferation, e.g., cancer, inhibition of CAP-dependent translation initiation prevents cellular proliferation. Described herein are molecules that specifically interact and disrupt the eIF4E/eIF4g interaction, thereby selectively preventing CAP-dependent translation initiation, thereby identifying the described molecules as cytotoxic to proliferating cells. Inhibitors of 3IF4E can be targeted, for example, for their ability to disrupt the eIF4E/eiF4G interaction, or for their ability to enhance an eIF4E/4E-BP interaction (4E-BP's (binding proteins) bind to eIF4E and block eIF4G binding).

In one embodiment, the disclosure is directed to a compound of Formula I:

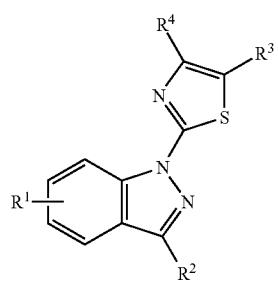

Formula I wherein, $R^1$ is selected from the group consisting of: an alkyl, haloalkyl, halide, Cl, $CF_3$, $CHF_2$, alkoxy, aryl, sulfone, sulfoxide, nitrile, carboxy, carboxamide, carbamate, urethane, amide, sulfamide, cyclic alkyl, amino and optionally substituted versions thereof; $R^2$ is selected from the group consisting of: a carboxy, hydroxy, amino, aminocarboxamide, aryl, heteroaryl, alkyl, alkylcarboxy, alkylcarboxamide and optionally substituted versions thereof; $R^3$ is selected from the group consisting of: H, alkyl, halo, haloalkyl, aryl, heteroaryl, hydroxyl, amino or substituted amino; and $R^4$ is selected from the group consisting of: an aryl, substituted aryl and a substituent of Table II. In a particular embodiment, $R^4$ is

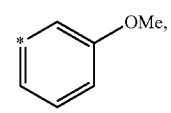

wherein the group is attached at the (*). In a particular embodiment, the compound is selected from the group consisting of the structures in Table IV and FIG. 16. In a particular embodiment, $R^4$ is H when $R^3$ is an aryl.

In one embodiment, the disclosure is directed to a compound of Formula II:

Formula II wherein, $R^1$ is selected from the group consisting of: an alkyl, haloalkyl, halide, Cl, $CF_3$, $CHF_2$, alkoxy, aryl, sulfone, sulfoxide, nitrile, carboxy, carboxamide, carbamate, urethane, amide, sulfamide, cyclic alkyl, amino and optionally substituted versions thereof; $R^{2'}$ is selected from the group consisting of: carboxy, hydroxy, amino, aminocarboxamide, aryl, heteroaryl, alkyl, alkylcarboxy, alkylcarboxamide, a structure described in Table I and optionally substituted versions thereof; $R^3$ is selected from the group consisting of: H, alkyl, halo, haloalkyl, aryl, heteroaryl, hydroxyl, amino or substituted amino; and $R^4$ is selected from the group consisting of: an aryl, substituted aryl and a substituent of Table II. In a particular embodiment, $R^4$ is

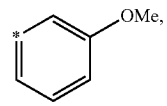

wherein the group is attached at the (*).

In one embodiment, the disclosure is directed to a compound of Formula III:

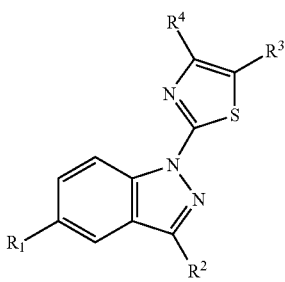

Formula III wherein, $R^1$ is selected from the group consisting of: an alkyl, haloalkyl, halide, Cl, $CF_3$, $CHF_2$, alkoxy, aryl, sulfone, sulfoxide, nitrile, carboxy, carboxamide, carbamate, urethane, amide, sulfamide, cyclic alkyl, amino and optionally substituted versions thereof; $R^2$ is selected from the group consisting of: a carboxy, hydroxy, amino, aminocarboxamide, aryl, heteroaryl, alkyl, alkylcarboxy, alkylcarboxamide and optionally substituted versions thereof; $R^3$ is selected from the group consisting of: H, alkyl, halo, haloalkyl, aryl, heteroaryl, hydroxyl, amino or substituted amino; and $R^4$ is selected from the group consisting of: an aryl, substituted aryl and a substituent of Table II. In a particular embodiment, $R^4$ is

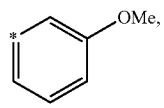

wherein the group is attached at the (*). In a particular embodiment, $R^1$ is selected from the group consisting of: CN, $CF_3$ and Cl.

In one embodiment, the disclosure is directed to a compound of Formula IV:

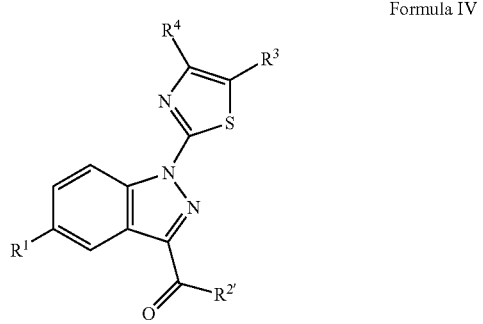

Formula IV wherein, $R^1$ is selected from the group consisting of: an alkyl, haloalkyl, halide, Cl, $CF_3$, $CHF_2$, alkoxy, aryl, sulfone, sulfoxide, nitrile, carboxy, carboxamide, carbamate, urethane, amide, sulfamide, cyclic alkyl, amino and optionally substituted versions thereof; $R^{2'}$ is selected from the group consisting of: carboxy, hydroxy, amino, aminocarboxamide, aryl, heteroaryl, alkyl, alkylcarboxy, alkylcarboxamide, a structure described in Table I and optionally substituted versions thereof; $R^3$ is selected from the group consisting of: H, alkyl, halo, haloalkyl, aryl, heteroaryl, hydroxyl, amino or substituted amino; and $R^4$ is selected from the group consisting of: an aryl, substituted aryl and a substituent of Table II. In a particular embodiment, $R^4$ is

*⟨OMe⟩ wherein the group is attached at the (*).

One embodiment is directed to a method of treating or preventing a hyperproliferative disorder or a neurological disease or disorder comprising administering an effective amount of a compound described herein. In a particular embodiment, the subject is diagnosed with or is at risk of developing a hyperproliferative disorder or a neurological disease or disorder. In a particular embodiment, the hyperproliferative disorder is cancer. In a particular embodiment, the compound is administered in combination with another therapeutic agent.

One embodiment is directed to a pharmaceutical composition comprising a compound described herein.

One embodiment is directed to the use of a compound or formulation as provided herein for the production of a medicament for the treatment or prevention of a hyperproliferative disorder, a neurodegenerative disease or disorder, or autism. In a particular embodiment, the hyperproliferative disorder is cancer. In a particular embodiment, the neurodegenerative disorder is Alzheimer's disease or Parkinson's disease.

One embodiment is directed to a method of treating or preventing a neurodegenerative disease or disorder comprising administering an effective amount of a compound described herein. In a particular embodiment, the subject is diagnosed with or is at risk of developing a neurodegenerative disease or disorder. In a particular embodiment, the neurodegenerative disease or disorder is Alzheimer's disease or Parkinson's disease. In a particular embodiment, the compound is administered in combination with another therapeutic agent.

One embodiment is directed to a method of treating or preventing a disease or disorder of the autism spectrum comprising administering an effective amount of a compound described herein. In a particular embodiment, the subject is diagnosed with or is at risk of developing a disease or disorder of the autism spectrum. In a particular embodiment, the disease or disorder is autism. In a particular embodiment, the compound is administered in combination with another therapeutic agent.

BRIEF DESCRIPTION OF THE DRAWINGS

FIG. 1A shows the process for synthesis of the indazole acid. FIG. 1B shows the process for the synthesis of a chlorothiazole intermediate. FIG. 1C shows the process for the final stage of Structure 2 synthesis.

DETAILED DESCRIPTION

Figure 1A:
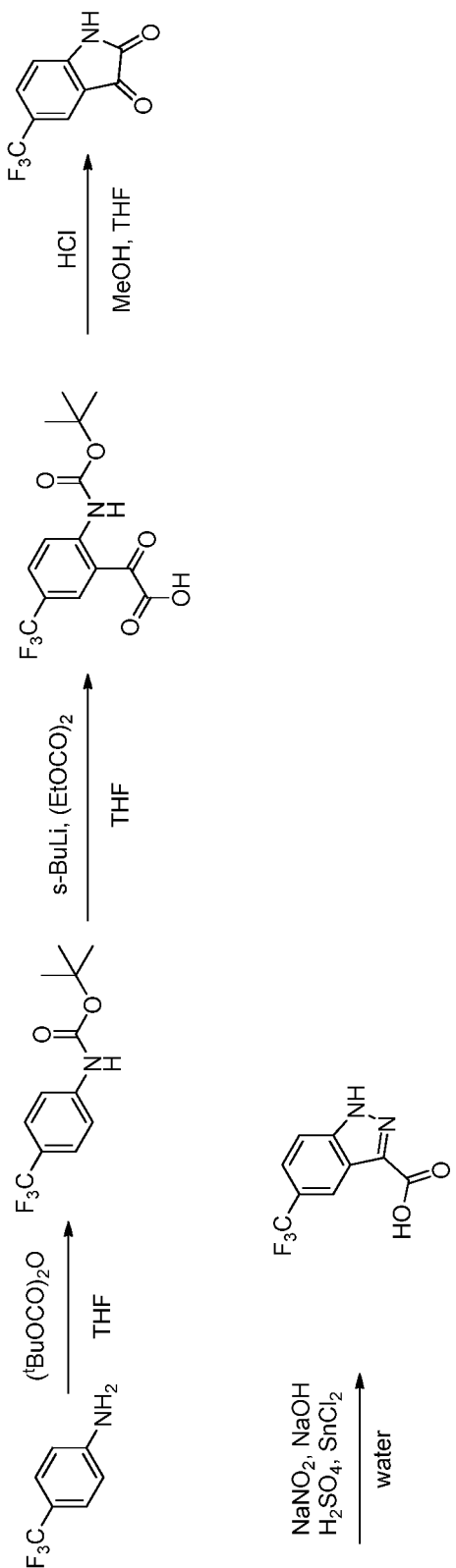
FIGS. 1A-C are a series of schematics showing various stages during the synthesis of Structure 1 and precursors.

Described herein are compositions, methods for using compositions, methods of identifying and designing compositions, and therapeutic formulations for the treatment of a cellular proliferative disorder (e.g., cancer), a neurological disease or disorder (e.g., Alzheimer's disease) or a disease or disorder from the autism spectrum (e.g., autism). The compositions and methods described herein are designed to modulate translation initiation through an interaction with the translation initiation factor 4E (eIF4E). As aberrant translation initiation is a hallmark of hyperproliferative disorders, neurological disorders and disorders from the autism spectrum, modulating the activity of eIF4E and complexes comprising eIF4E presents an effective target for treating such disorders.

As used herein, a "proliferative disease or disorder," "cellular proliferative disease or disorder," or "hyperproliferative disease or disorder" refer to a condition in a subject where cells exhibit abnormal proliferation. "Hyperproliferative" diseases or disorders are such that cells proliferate at rates higher than in a non-disease or non-disorder state. Neoplastic tissues comprise cells that are hyperproliferative, for example. Cancer and tumorigenesis also exhibit cellular hyperproliferation. As described herein, hyperproliferative diseases driven by eIF4E-dependent translation (e.g., PI3K, Akt, mTOR, Ras, MAPK, MNK or Myc pathways) can be treated by the compounds and methods described herein.

The term "cancer" refers to or describes the physiological condition that is typically characterized by unregulated cell growth, i.e., hyperproliferation. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer, carcinoma of the lung and squamous carcinoma of the lung, HPV-related cancers, cancer of the peritoneum, hepatocellular cancer, gastric or stomach cancer including gastrointestinal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, multiple myeloma, acute myeloid leukemia, and B-cell lymphoma, brain, as well as head and neck cancer, and associated metastases.

As used herein, a "neurological disease or disorder" refers to any disorder of the nervous system. Examples of symptoms include paralysis, muscle weakness, poor coordination, loss of sensation, seizures, confusion, pain and altered levels of consciousness. There are many recognized neurological disorders, some relatively common, but many rare. Neurological disorders include, for example, Alzheimer's disease, aphasia, apraxia, arachnoiditis, ataxia telangiectasia, attention deficit hyperactivity disorder, auditory processing disorder, autism, Bell's palsy, brachial plexus injury, brain damage, brain injury, brain tumor, canavan disease, carpal tunnel syndrome, causalgia, central pain syndrome, central pontine myelinolysis, centronuclear myopathy, cephalic disorder, cerebral aneurysm, cerebral arteriosclerosis, cerebral atrophy, cerebral gigantism, cerebral palsy, cerebral vasculitis, cervical spinal stenosis, Charcot-Marie-Tooth disease, Chiari malformation, chorea, chronic fatigue syndrome, chronic inflammatory demyelinating polyneuropathy (CIDP), chronic pain, Coffin-Lowry syndrome, coma, complex regional pain syndrome, compression neuropathy, congenital facial diplegia, corticobasal degeneration, cranial arteritis, craniosynostosis, Creutzfeldt-Jakob disease, cumulative trauma disorders, Cushing's syndrome, cytomegalic inclusion body disease (CIBD), cytomegalovirus Infection, Dandy-Walker syndrome, Dawson disease, DeMorsier's syndrome, Dejerine-Klumpke palsy, Dejerine-Sottas disease, delayed sleep phase syndrome, dementia, dermatomyositis, developmental dyspraxia, diabetic neuropathy, diffuse sclerosis, Dravet syndrome, dysautonomia, dyscalculia, dysgraphia, dyslexia, dystonia, empty sella syndrome, encephalitis, encephalocele, encephalotrigeminal angiomatosis, encopresis, epilepsy, Erb's palsy, erythromelalgia, essential tremor, Fabry's disease, Fahr's syndrome, fainting, familial spastic paralysis, febrile seizures, Fisher syndrome, Friedreich's ataxia, fibromyalgia, Foville's syndrome, Gaucher's disease, Gerstmann's syndrome, giant cell arteritis, giant cell inclusion disease, globoid cell leukodystrophy, gray matter heterotopia, Guillain-Barré syndrome, HTLV-1 associated myelopathy, Hallervorden-Spatz disease, headache, hemifacial spasm, hereditary spastic paraplegia, heredopathia atactica polyneuritiformis, herpes zoster oticus, herpes zoster, Hirayama syndrome, holoprosencephaly, Huntington's disease, hydranencephaly, hydrocephalus, hypercortisolism, hypoxia, immune-mediated encephalomyelitis, inclusion body myositis, incontinentia pigmenti, infantile phytanic acid storage disease, infantile refsum disease, infantile spasms, inflammatory myopathy, intracranial cyst, intracranial hypertension, Joubert syndrome, Karak syndrome, Kearns-Sayre syndrome, Kennedy disease, Kinsbourne syndrome, Klippel Feil syndrome, Krabbe disease, Kugelberg-Welander disease, kuru, Lafora disease, Lambert-Eaton myasthenic syndrome, Landau-Kleffner syndrome, lateral medullary (Wallenberg) syndrome, learning disabilities, Leigh's disease, Lennox-Gastaut syndrome, Lesch-Nyhan syndrome, leukodystrophy, Lewy body dementia, lissencephaly, locked-in syndrome, Lou Gehrig's disease, lumbar disc disease, lumbar spinal stenosis, Lyme disease, Machado-Joseph disease (Spinocerebellar ataxia type 3), macrencephaly, macropsia, megalencephaly, Melkersson-Rosenthal syndrome, Menieres disease, meningitis, Menkes disease, metachromatic leukodystrophy, microcephaly, micropsia, migraine, Miller Fisher syndrome, mini-stroke (transient ischemic attack), misophonia, mitochondrial myopathy, Mobius syndrome, monomelic amyotrophy, motor neurone disease, motor skills disorder, moyamoya disease, mucopolysaccharidoses, multi-infarct dementia, multifocal motor neuropathy, multiple sclerosis, multiple system atrophy, muscular dystrophy, myalgic encephalomyelitis, myasthenia gravis, myelinoclastic diffuse sclerosis, myoclonic encephalopathy of infants, myoclonus, myopathy, myotubular myopathy, myotonia congenital, narcolepsy, neurofibromatosis, neuroleptic malignant syndrome, neurological manifestations of AIDS, neurological sequelae of lupus, neuromyotonia, neuronal ceroid lipofuscinosis, neuronal migration disorders, Niemann-Pick disease, non-24-hour sleep-wake syndrome, nonverbal learning disorder, O'Sullivan-McLeod syndrome, occipital neuralgia, occult spinal dysraphism sequence, Ohtahara syndrome, olivopontocerebellar atrophy, opsoclonus myoclonus syndrome, optic neuritis, orthostatic hypotension, overuse syndrome, palinopsia, panic disorder, paresthesia, Parkinson's disease, paramyotonia congenital, paraneoplastic diseases, paroxysmal attacks, Parry-Romberg syndrome, Pelizaeus-Merzbacher disease, periodic paralyses, peripheral neuropathy, pervasive developmental disorders, photic sneeze reflex, phytanic acid storage disease, Pick's disease, pinched nerve, pituitary tumors, PMG, polio, polymicrogyria, polymyositis, porencephaly, post-polio syndrome, postherpetic neuralgia (PHN), postural hypotension, Prader-Willi syndrome, primary lateral sclerosis, prion diseases, progressive hemifacial atrophy, progressive multifocal leukoencephalopathy, progressive supranuclear palsy, pseudotumor cerebri, rabies, Ramsay Hunt syndrome type I, Ramsay Hunt syndrome type II, Ramsay Hunt syndrome type III, Rasmussen's encephalitis, reflex neurovascular dystrophy, refsum disease, repetitive stress injury, restless legs syndrome, retrovirus-associated myelopathy, Rett syndrome, Reye's syndrome, rhythmic movement disorder, Romberg syndrome, Saint Vitus dance, Sandhoff disease, schizophrenia, Schilder's disease, schizencephaly, sensory integration dysfunction, septo-optic dysplasia, shaken baby syndrome, shingles, Shy-Drager syndrome, Sjögren's syndrome, sleep apnea, sleeping sickness, snatiation, Sotos syndrome, spasticity, spina bifida, spinal cord injury, spinal cord tumors, spinal muscular atrophy, spinocerebellar ataxia, Steele-Richardson-Olszewski syndrome, stiff person syndrome, stroke, Sturge-Weber syndrome, subacute sclerosing panencephalitis, subcortical arteriosclerotic encephalopathy, superficial siderosis, Sydenham's chorea, syncope, synesthesia, syringomyelia, tarsal tunnel syndrome, tardive dyskinesia, tardive dysphrenia, tarlov cyst, Tay-Sachs disease, temporal arteritis, tetanus, tethered spinal cord syndrome, Thomsen disease, thoracic outlet syndrome, tic douloureux, Todd's paralysis, Tourette's syndrome, toxic encephalopathy, transient ischemic attack, transmissible spongiform encephalopathies, transverse myelitis, traumatic brain injury, tremor, trigeminal neuralgia, tropical spastic paraparesis, trypanosomiasis, tuberous sclerosis, ubisiosis, Von Hippel-Lindau disease (VHL), Viliuisk encephalomyelitis (VE), Werdnig-Hoffman disease, West syndrome, whiplash, Williams syndrome and Wilson's disease.

The compositions and methods described herein are useful, for example, to treat Alzheimer's disease and or to ameliorate symptoms associated with Alzheimer's disease. Alzheimer's disease has been demonstrated to be caused by aberrant CAP-dependent translation initiation, and can be treated by eIF4E inhibitor(s) (Bottley, A. et al., *PLoS One*, 5:pii e13030, 2010).

As used herein, the "autism spectrum" refers to a range of conditions classified as pervasive developmental disorders in the Diagnostic and Statistical Manual of Mental Disorders (DSM). Pervasive developmental disorders include autism, Asperger syndrome, pervasive developmental disorder not otherwise specified (PDD-NOS), childhood disintegrative disorder, and Rett syndrome. These disorders are typically characterized by social deficits, communication difficulties, stereotyped or repetitive behaviors and interests, and in some cases, cognitive delays. Although these diagnoses share some common features, individuals with these disorders are thought to be "on the spectrum" because of differences in severity across these domains.

As used herein, "autism" refers to a developmental disorder characterized by delays or abnormal functioning before the age of three years in one or more of the following domains: (1) social interaction; (2) communication; and (3) restricted, repetitive, and stereotyped patterns of behavior, interests, and activities. Social impairments are marked by poor use of nonverbal communication, difficulty in peer relations, lack of social-emotional reciprocity, and lack of shared enjoyment. Communication deficits include failure to develop speech, use of stereotyped or delayed echolalia, and difficulties maintaining conversations. Social and communication impairments cause a lack of symbolic or imaginative play. Restricted and repetitive behaviors include unusual preoccupations with narrow interests, inflexibility to nonfunctional routines, stereotyped and repetitive mannerisms, and preoccupations with parts of objects. Autism has been shown to be linked to misregulated translation initiation, which can be ameliorated by inhibiting, for example, eIF4E (Neves-Pereira, M. et al., *J. Med. Genet.*, 46:759-65, 2009; Gkogkas, C. et al., *Nature*, 493:371-7, 2013; Santini, et al., *Nature*, 493:411-5, 2013).

The compositions and methods described herein are useful, for example, to treat Parkinson's disease and or to ameliorate symptoms associated with Parkinson's disease. Parkinson's disease has been demonstrated to be caused by aberrant CAP-dependent translation initiation, and can be treated by eIF4E inhibitor(s) (Garber, K., *J. Natl. Cancer Inst.*, 102:371-4, 2010; Devine, M. et al., *Nat. Rev. Cancer*, 11:812-23, 2011; Santini, E. et al., *Sci. Signal.*, 2:ra36, 2009; Kong, J. & Lasko, P., *Nat. Rev. Genet.*, 13:383-94, 2012).

As used herein, "tumor" refers to neoplastic cell growth and proliferation, whether malignant or benign, and all precancerous and cancerous cells and tissues.

A hallmark of hyperproliferation, certain neurological disorders and disorders of the autism spectrum, is the need for CAP-dependent translation. Increased proliferation, for example, requires increased protein synthesis. CAP-dependent translation is initiated by a translation initiation complex, eIF4F, comprising factors eIF4E and eIF4G. The interaction of eIF4E and eIF4G is necessary for CAP-dependent translation initiation. This interaction is attenuated endogenously by 4E binding protein(s) (4E-BP), and, therefore, a compound that enhances the binding of eIF4E to 4E-BP would also function as an inhibitor (Jacobson, B. et al., *Cancer Res.*, 66:4256-4262, 2006).

Molecules that inhibit eIF4E, e.g., 4EGI-1, have some anti-proliferative properties (Moerke, N. et al., *Cell*, 128:257-67, 2007; Chen, L. et al., *Oncotarget*, 3:869-81, 2012).

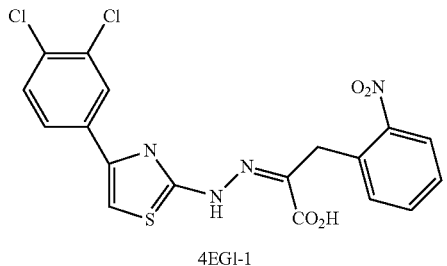

4EGI-1

As used herein, "eIF4E" refers to the eukaryotic translation initiation factor 4E. All eukaryotic cellular mRNAs are blocked at their 5-prime ends with a 7-methylguanosine cap structure, $m^7GpppX$ (where X is any nucleotide). This structure is involved in several cellular processes including enhanced translational efficiency, splicing, mRNA stability and RNA nuclear export. eIF4E is a eukaryotic translation initiation factor involved in directing ribosomes to the cap structure of mRNAs. It is a 24 kD polypeptide that exists as both a free form and as part of a multiprotein complex termed eIF4F. The eIF4E polypeptide is the rate-limiting component of the eukaryotic translation apparatus and is involved in the mRNA-ribosome binding step of eukaryotic protein synthesis. The other subunits of eIF4F are a 50 kD polypeptide, termed eIF4A (Nielsen, P. & Trachsel, H. *EMBO J.*, 7:2097-105, 1988), that possesses ATPase and RNA helicase activities, and a 220 kD polypeptide, eIF4G (Rychlik, W. et al., *Proc. Natl. Acad. Sci. USA*, 84:945-9, 1987). eIF4E plays a role in cellular growth regulation, as the overexpression of eIF4E causes malignant transformation (Jones, R. et al., *Somat. Cell Genet.*, 23:221-3, 1997).

The results described herein show the efficacy of compounds and formulations comprising substituted indazole compounds of the general formula depicted as Formulae I-IV.

Formula I

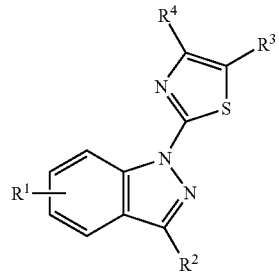

$R^1$ includes a range of substituents such as, for example, an alkyl, haloalkyl, halide, Cl, $CF_3$, $CHF_2$, alkoxy, aryl, sulfone, sulfoxide, nitrile, carboxy, carboxamide, carbamate, urethane, amide, sulfamide, cyclic alkyl, amino or optionally substituted versions thereof.

$R^2$ includes, for example, a substituent such as a carboxy, hydroxy, amino, aminocarboxamide, aryl, heteroaryl, alkyl, alkylcarboxyl, alkylcarboxamide or optionally substituted versions thereof.

$R^3$ can include, for example, a substituent such as H, alkyl, halo, haloalkyl, aryl, heteroaryl, hydroxyl, amino or substituted amino.

$R^4$ includes, for example, a substituent such as an aryl or substituted aryl (e.g., one listed in Table II). $R^4$ can be H when $R^3$ is aryl.

Formula II

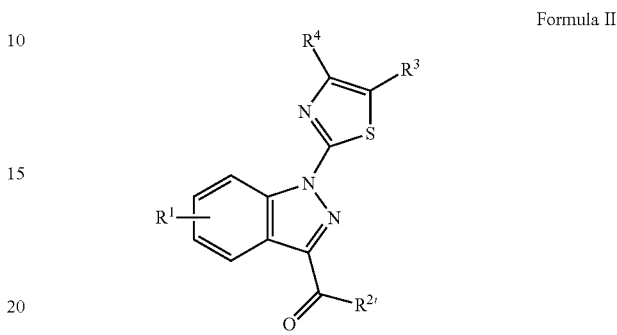

$R^1$ includes a range of substituents such as, for example, an alkyl, haloalkyl, halide, Cl, $CF_3$, $CHF_2$, alkoxy, aryl, sulfone, sulfoxide, nitrile, carboxy, carboxamide, carbamate, urethane, amide, sulfamide, cyclic alkyl, amino or optionally substituted versions thereof.

$R^{2'}$ can include, for example, a substituent such as an amino, substituted amino, aminosulfonamide, heteroaryl or aryl (Table I amines are examples).

$R^3$ can include, for example, a substituent such as H, alkyl, halo, haloalkyl, aryl, heteroaryl, hydroxyl, amino or substituted amino.

$R^4$ includes, for example, a substituent such as an aryl or substituted aryl (e.g., one listed in Table II). $R^4$ can be H when $R^3$ is aryl.

Formula III

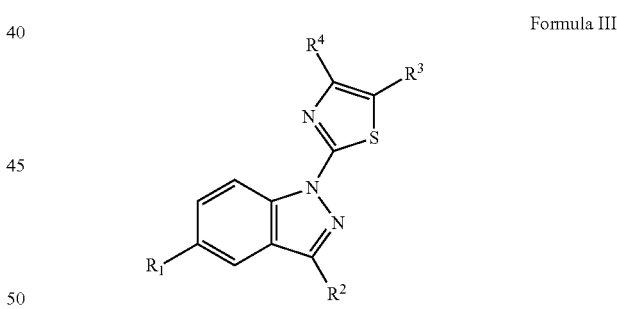

$R^1$ includes a range of substituents such as, for example, an alkyl, haloalkyl, halide, Cl, $CF_3$, $CHF_2$, alkoxy, aryl, sulfone, sulfoxide, nitrile, carboxy, carboxamide, carbamate, urethane, amide, sulfamide, cyclic alkyl, amino or optionally substituted versions thereof.

$R^2$ includes, for example, a substituent such as a carboxy, hydroxy, amino, aminocarboxamide, aryl, heteroaryl, alkyl, alkylcarboxy, alkylcarboxamide or optionally substituted versions thereof.

$R^3$ can include, for example, a substituent such as H, alkyl, halo, haloalkyl, aryl, heteroaryl, hydroxyl, amino or substituted amino.

$R^4$ includes, for example, a substituent such as an aryl or substituted aryl (e.g., one listed in Table II). $R^4$ can be H when $R^3$ is aryl.

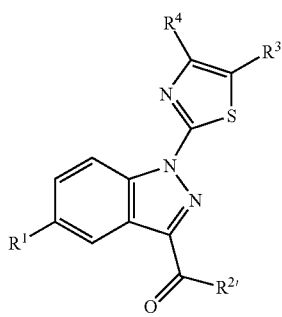

Formula IV

R[1] includes a range of substituents such as, for example, an alkyl, haloalkyl, halide, Cl, $CF_3$, $CHF_2$, alkoxy, aryl, sulfone, sulfoxide, nitrile, carboxy, carboxamide, carbamate, urethane, amide, sulfamide, cyclic alkyl, amino or optionally substituted versions thereof.

R[2'] can include, for example, a substituent such as an amino, substituted amino, aminosulfonamide, heteroaryl or aryl (Table I amines are examples).

R[3] can include, for example, a substituent such as H, alkyl, halo, haloalkyl, aryl, heteroaryl, hydroxyl, amino or substituted amino.

R[4] includes, for example, a substituent such as an aryl or substituted aryl (e.g., one listed in Table II). R[4] can be H when R[3] is aryl.

TABLE 1

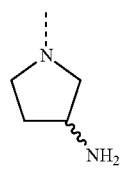

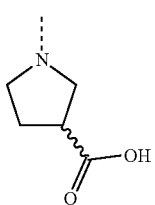

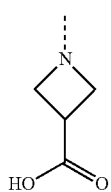

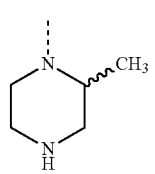

TABLE 1-continued

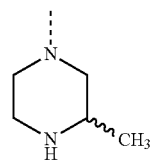

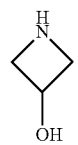

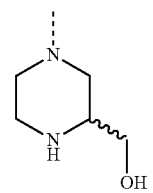

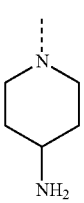

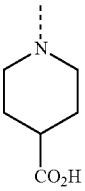

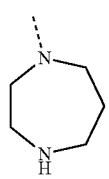

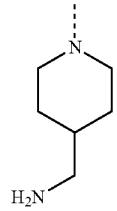

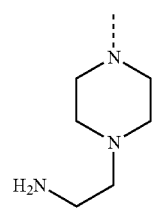

TABLE 1-continued
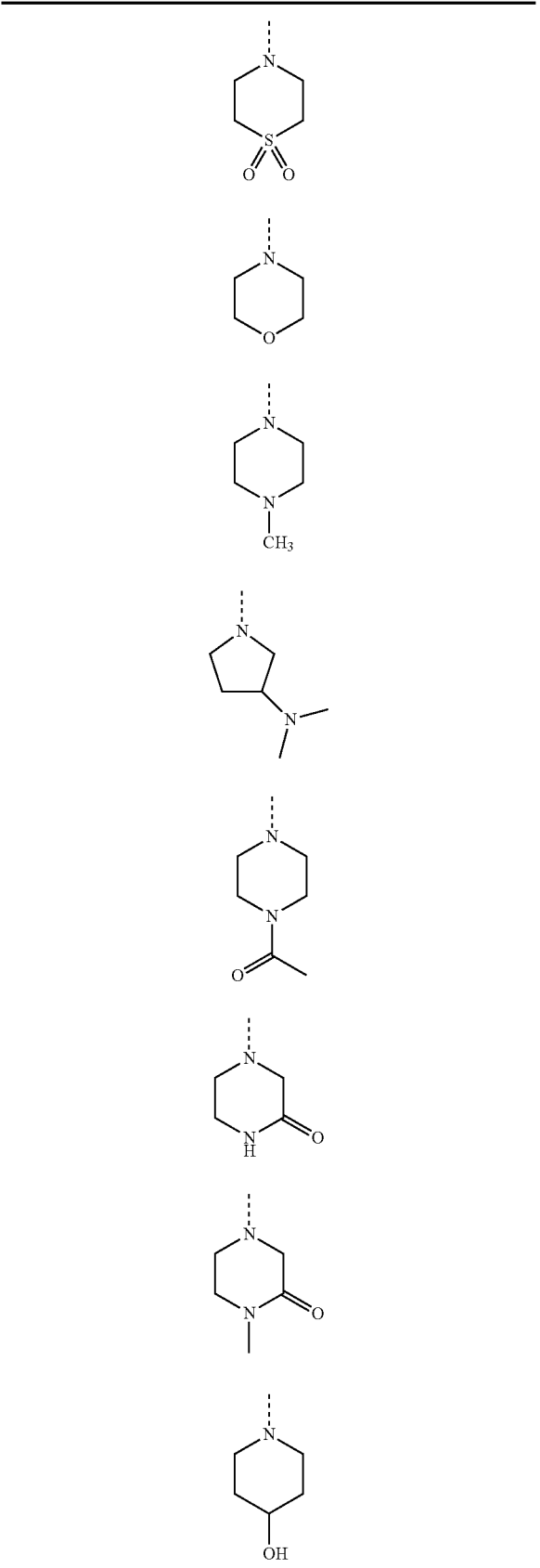
TABLE 1-continued
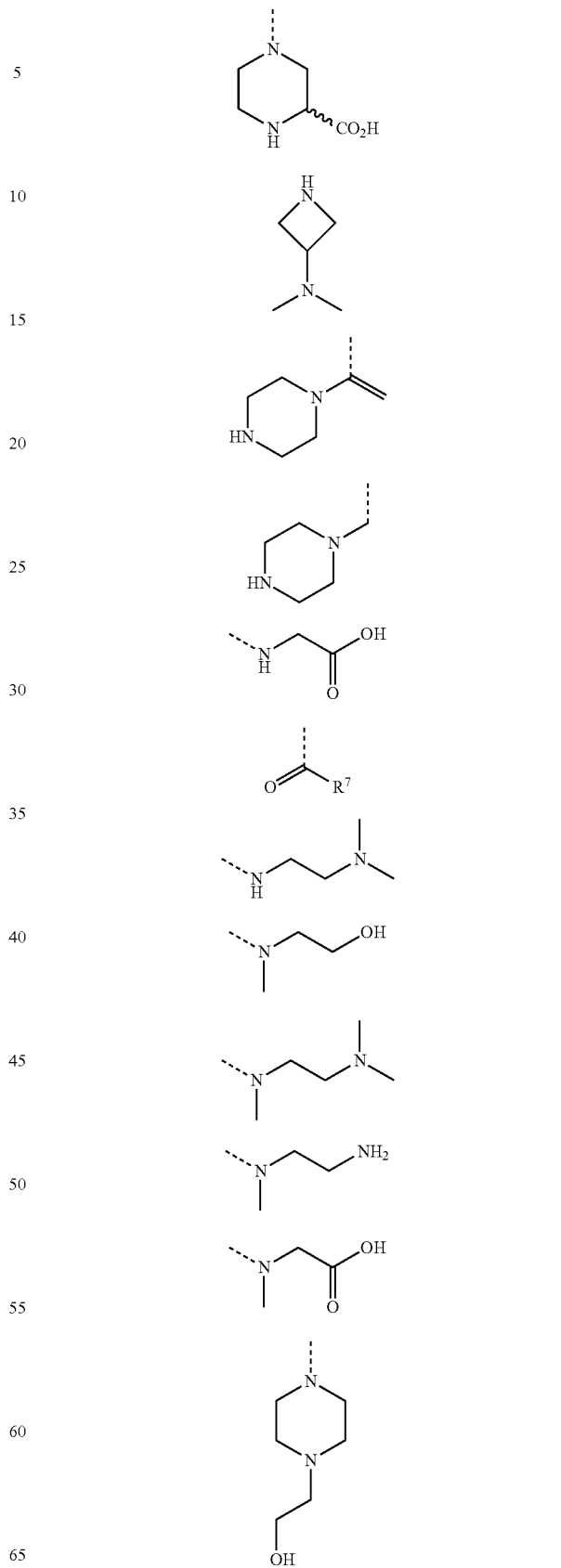

TABLE 1-continued
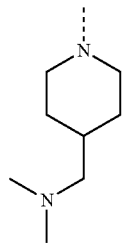
The dashed lines indicate the place of attachment.
TABLE II
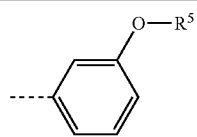
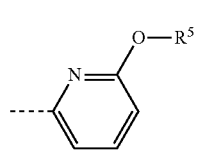
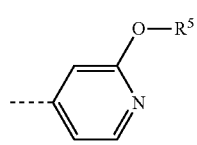
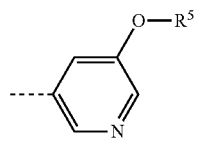
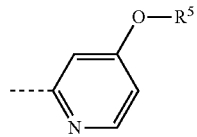
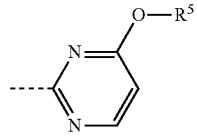
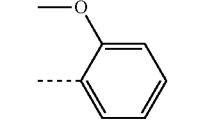
The dashed lines indicate the point of attachment.
Also disclosed herein are structures related to Formula I, wherein the substituted thiazole ring is replaced by another aromatic ring, e.g., a heteroaryl ring, see Table III.
TABLE III
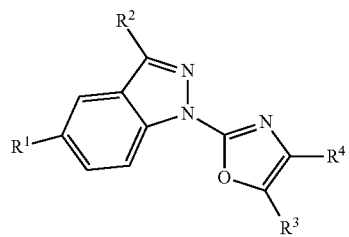
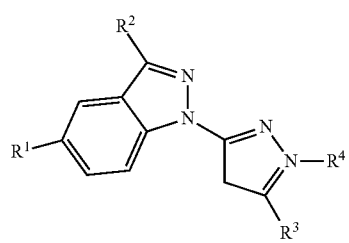
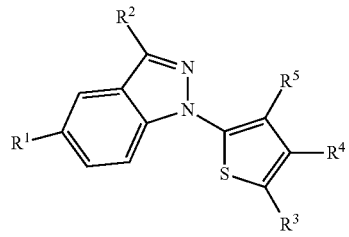
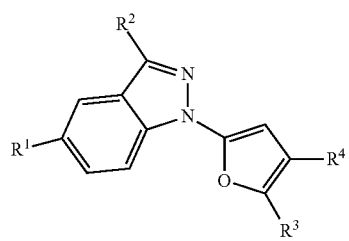
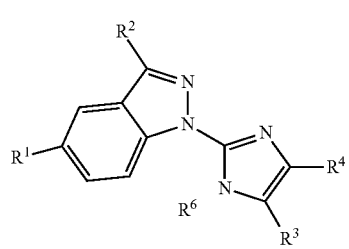
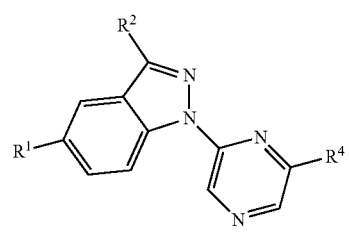

TABLE III-continued

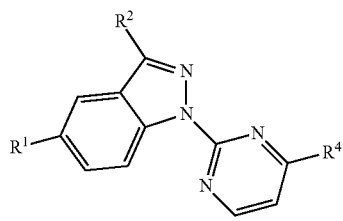

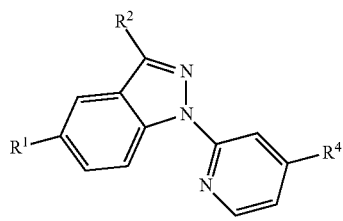

TABLE III-continued

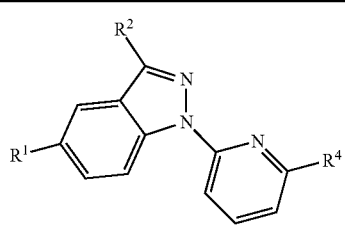

$R^5$ is typically H or a group that remains planar with the aromatic ring it is attached to. $R^6$ can be, for example, hydrogen, alkyl, haloalkyl, hydroxyl or alkoxy.

Figure 16:
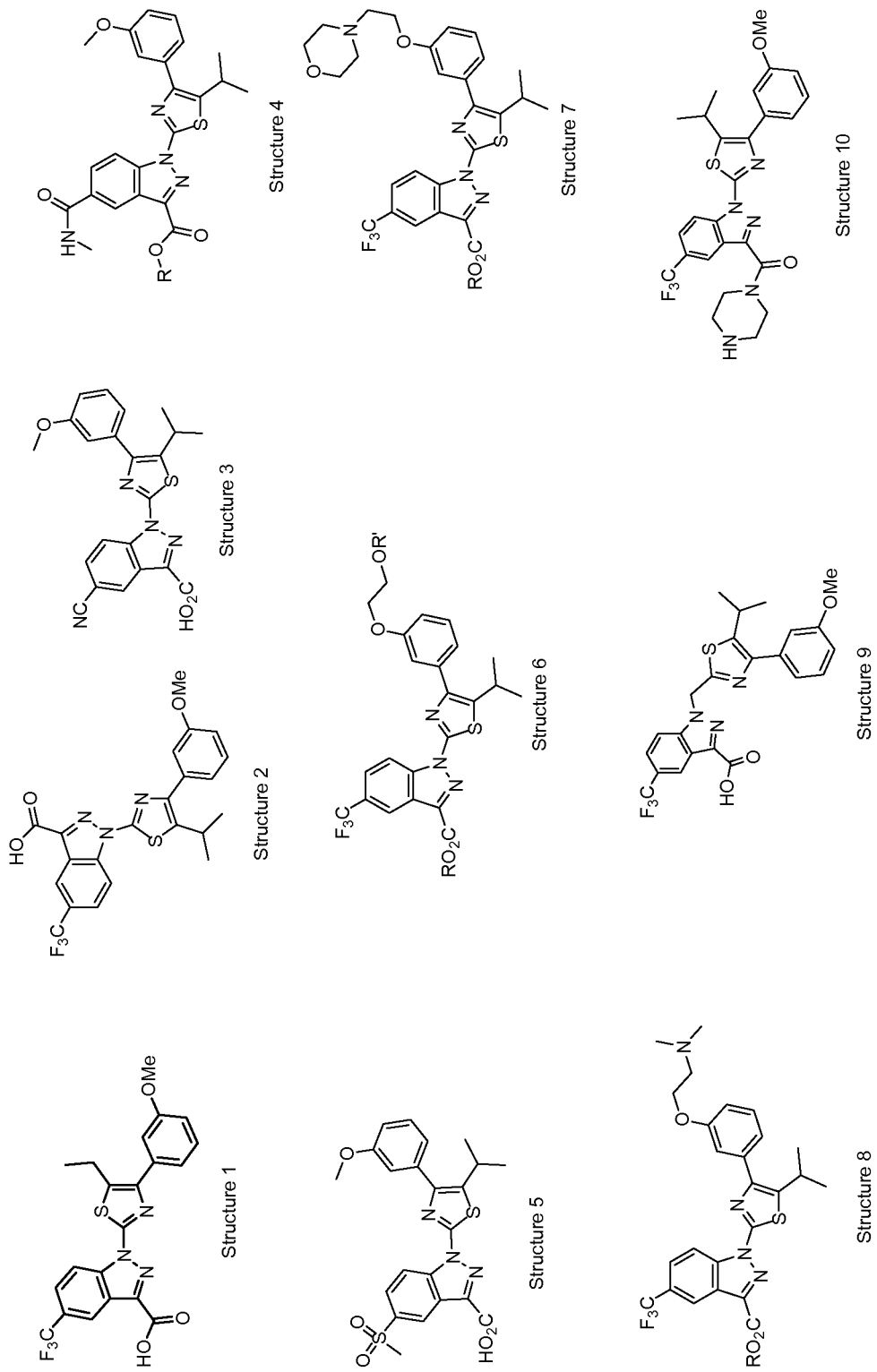
FIG. 16 is a series of chemical structures depicting Structures 1-10 as described herein.
Figure 17:
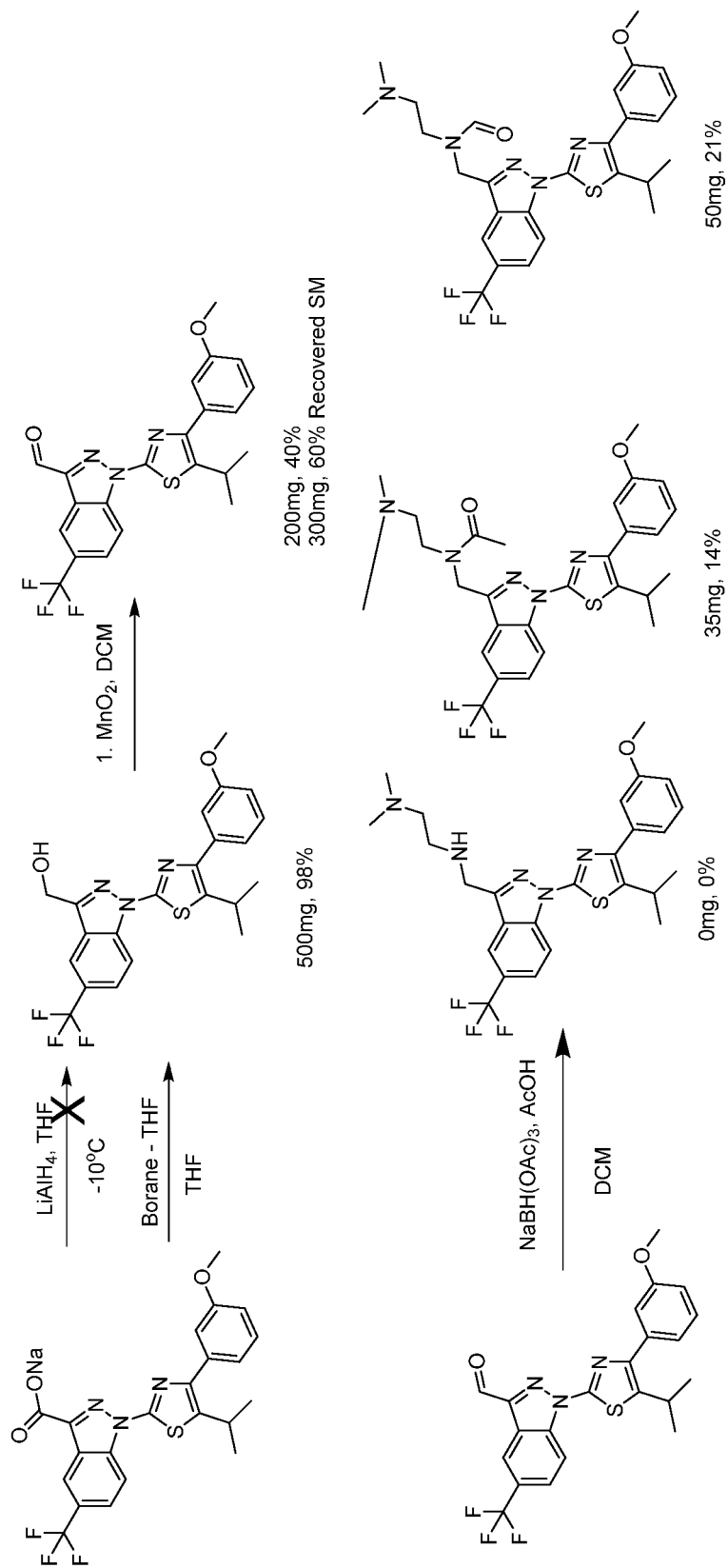
FIG. 17 shows a synthesis pathway for reduced amides described herein.
Figure 18:
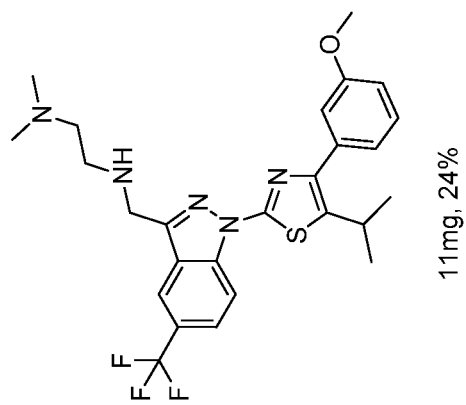
FIG. 18 shows a pathway for successful acidic hydrolysis to generate reduced amides described herein.
Figure 18:
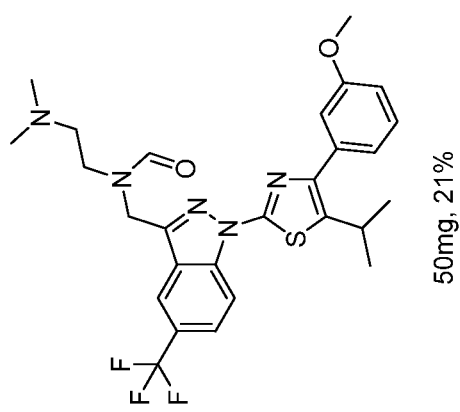
Figure 19:
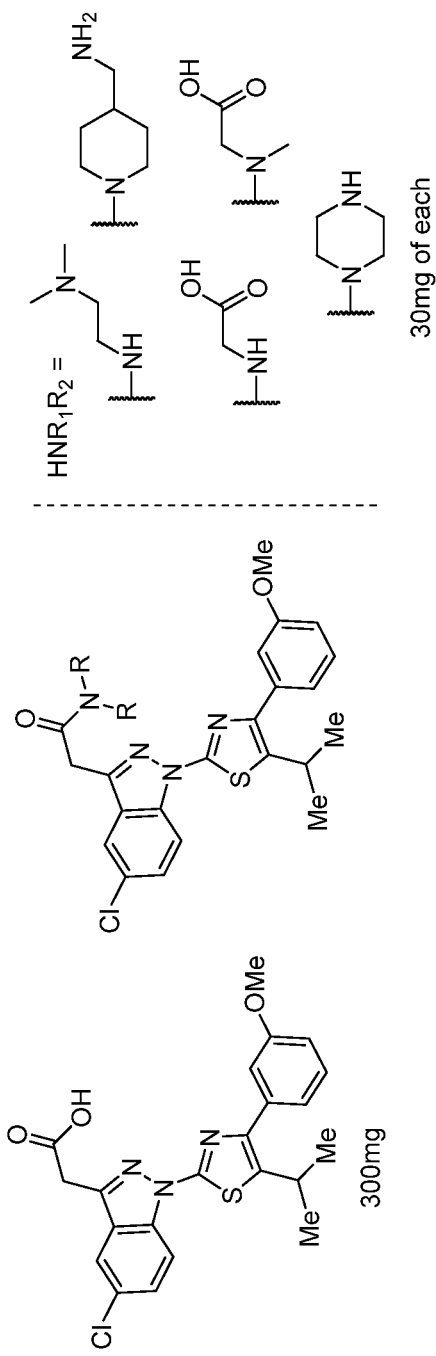
FIG. 19 shows structures and suitable R groups of indazole structures described herein.
Figure 20:
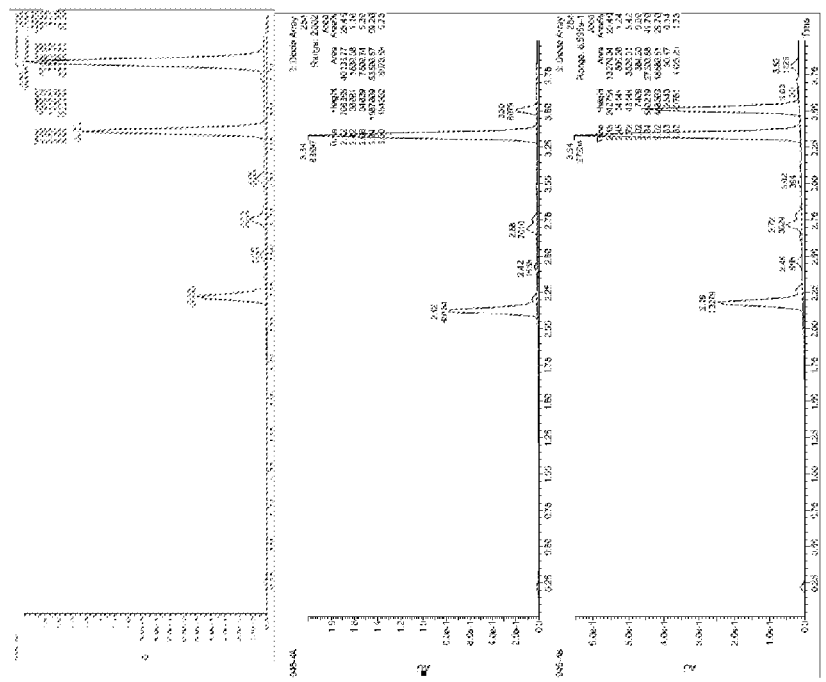
FIG. 20 shows structural data and synthesis pathways for structures described herein.
Figure 20:
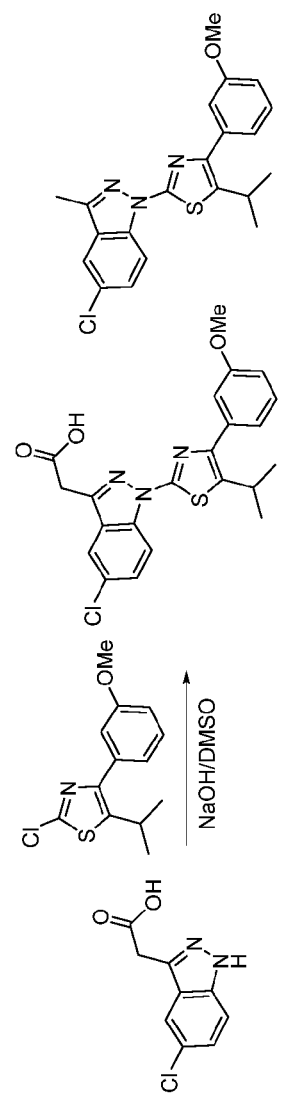
Figure 21:
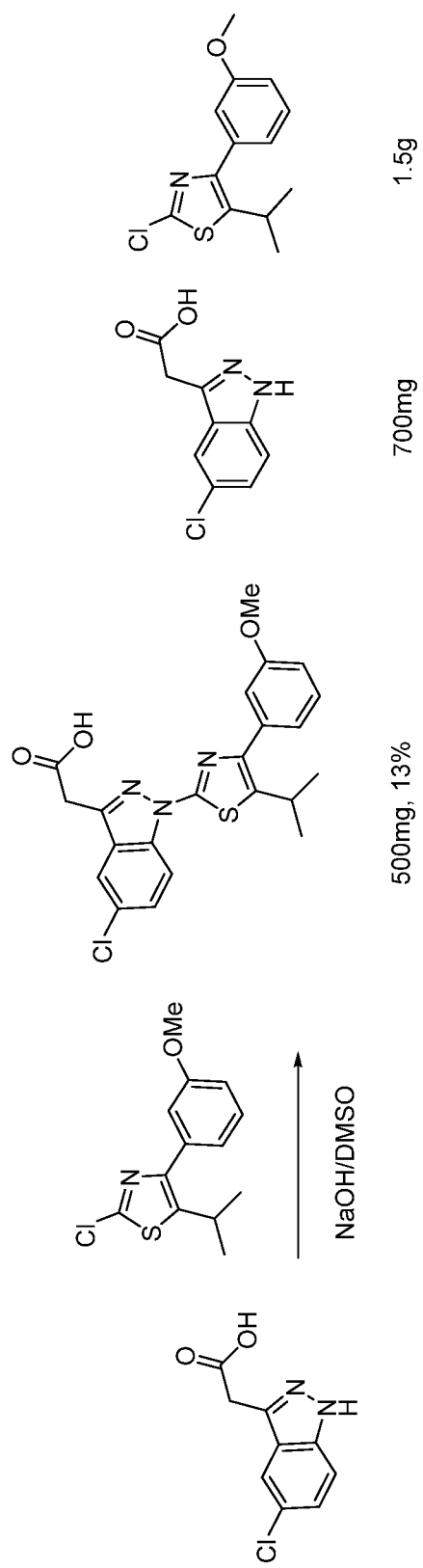
FIG. 21 shows synthesis and intermediates for compounds described herein.

Examples of specific structures are shown in FIG. 16 and in Table IV below. Structures 3 and 13-16 all showed activity in fluorescence polarization assays.

TABLE IV

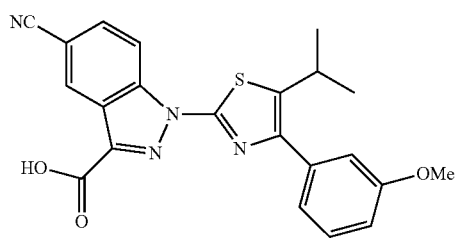 [SMILES: COc1cccc(-c2nc(-n3nc(C(=O)O)c4cc(C#N)ccc43)sc2C(C)C)c1]

Structure 3

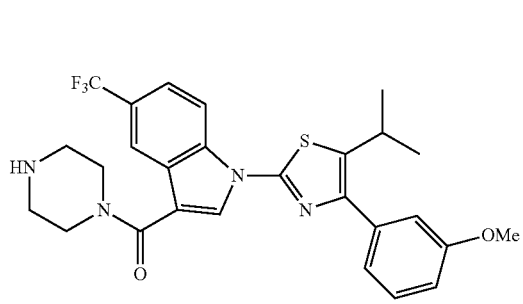 [SMILES: COc1cccc(-c2nc(-n3cc(C(=O)N4CCNCC4)c4cc(C(F)(F)F)ccc43)sc2C(C)C)c1]

Structure 10

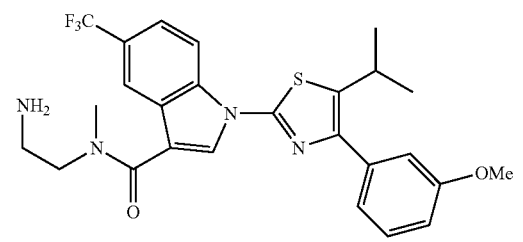 [SMILES: COc1cccc(-c2nc(-n3cc(C(=O)N(C)CCN)c4cc(C(F)(F)F)ccc43)sc2C(C)C)c1]

Structure 11

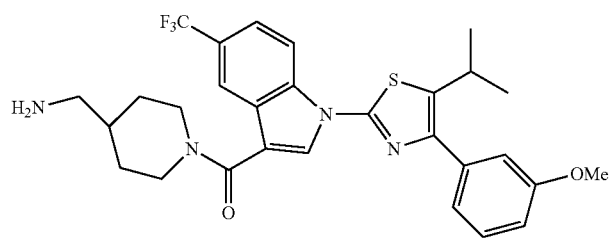 [SMILES: COc1cccc(-c2nc(-n3cc(C(=O)N4CCC(CN)CC4)c4cc(C(F)(F)F)ccc43)sc2C(C)C)c1]

Structure 12

TABLE IV-continued
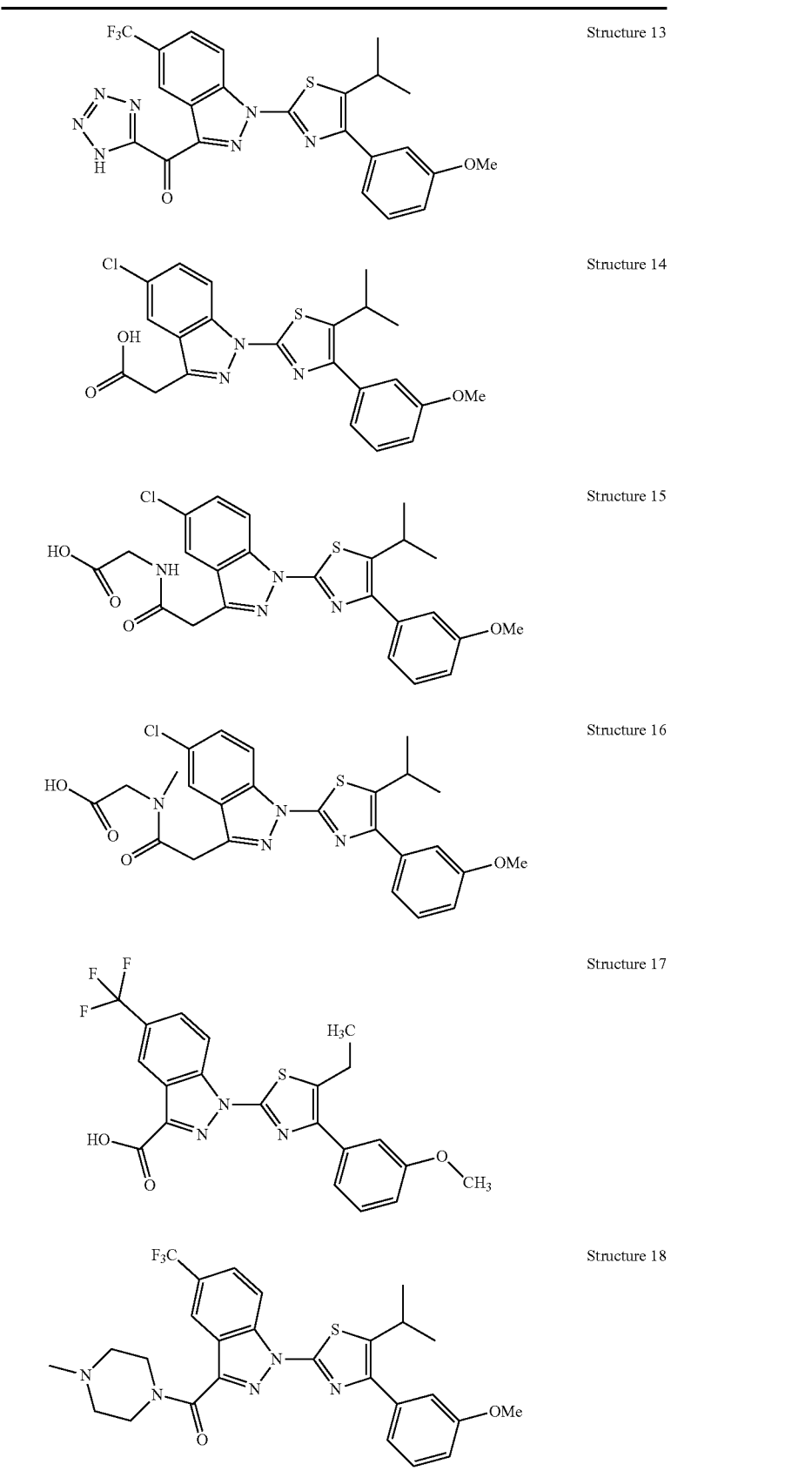
Structure 13
Structure 14
Structure 15
Structure 16
Structure 17
Structure 18

TABLE IV-continued
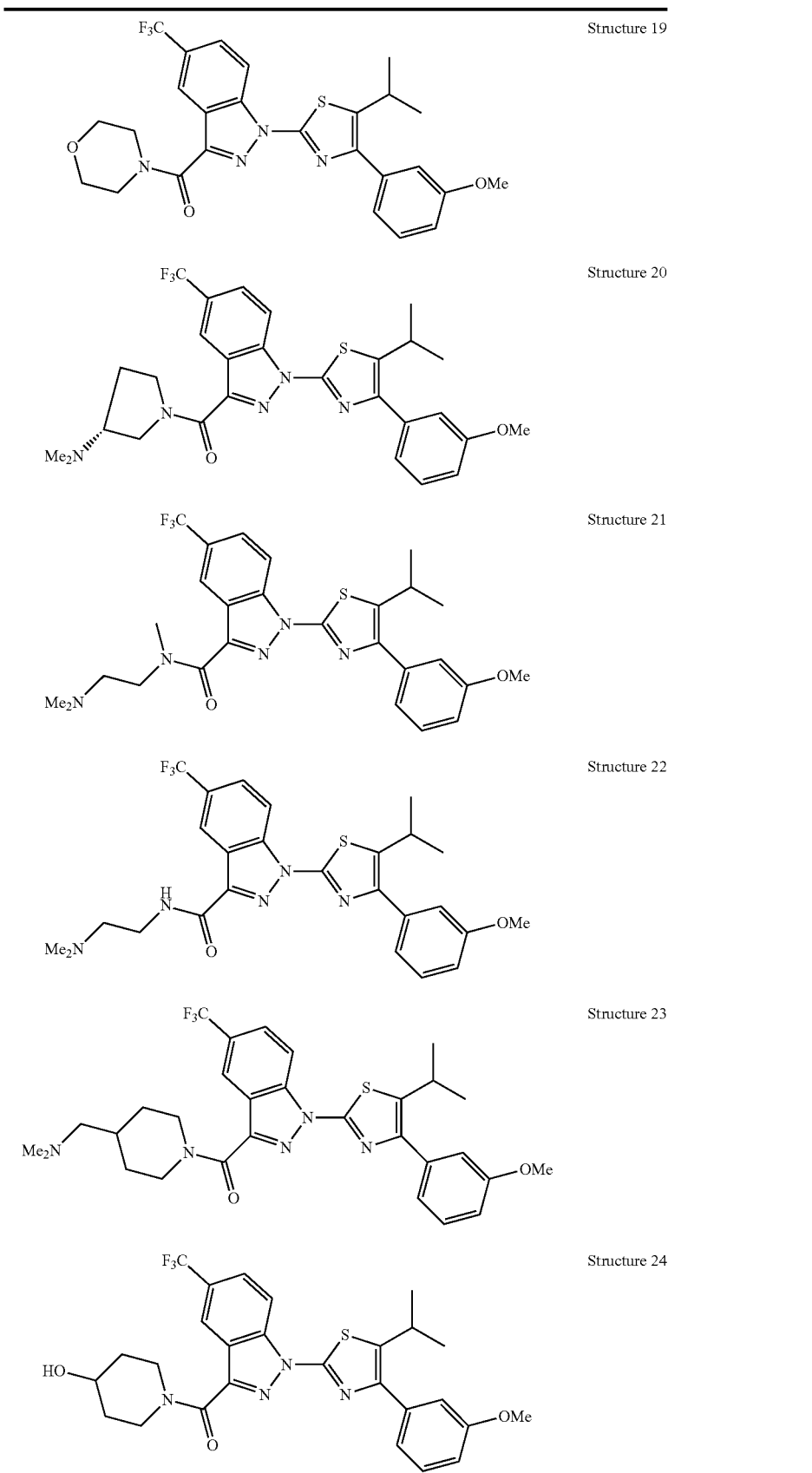
Structure 19
Structure 20
Structure 21
Structure 22
Structure 23
Structure 24

TABLE IV-continued
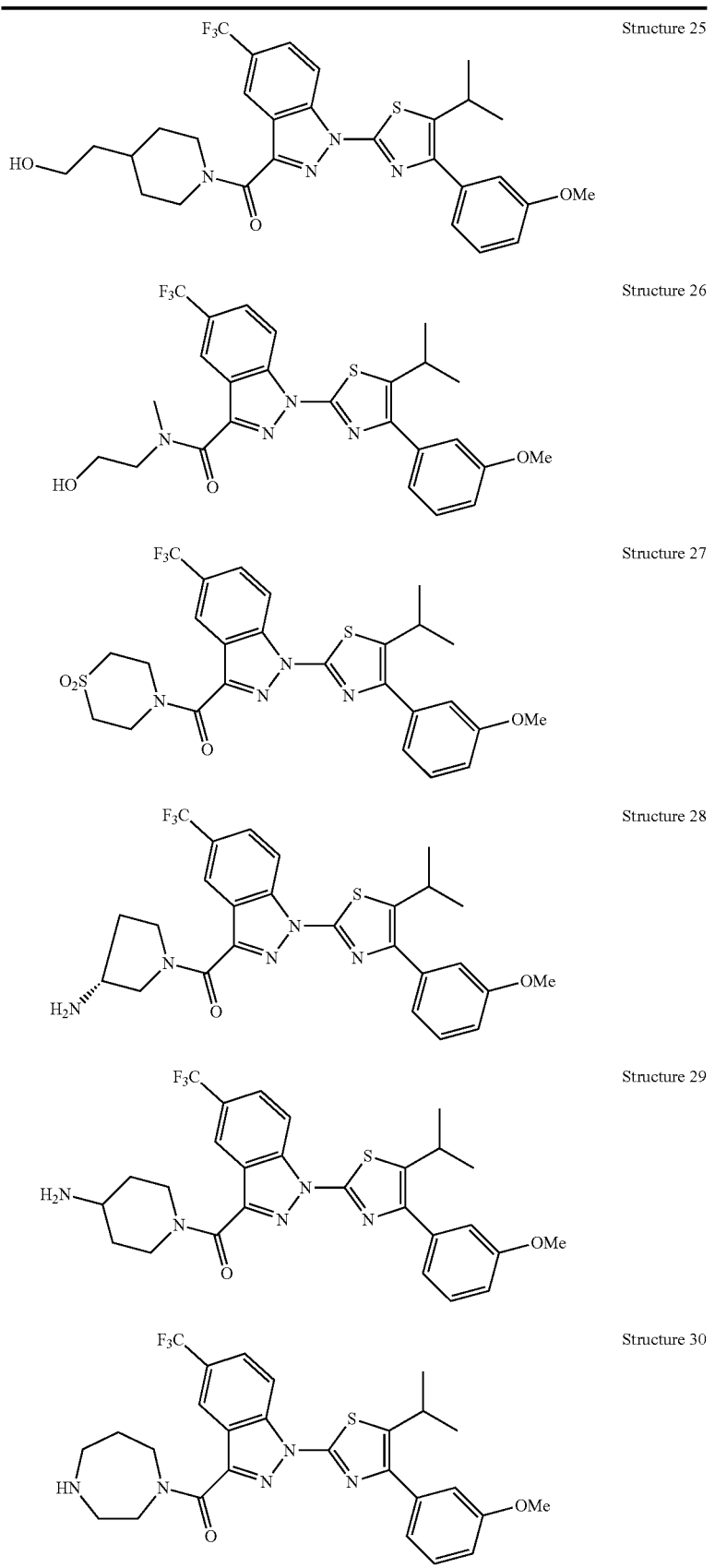
Structure 25
Structure 26
Structure 27
Structure 28
Structure 29
Structure 30

TABLE IV-continued
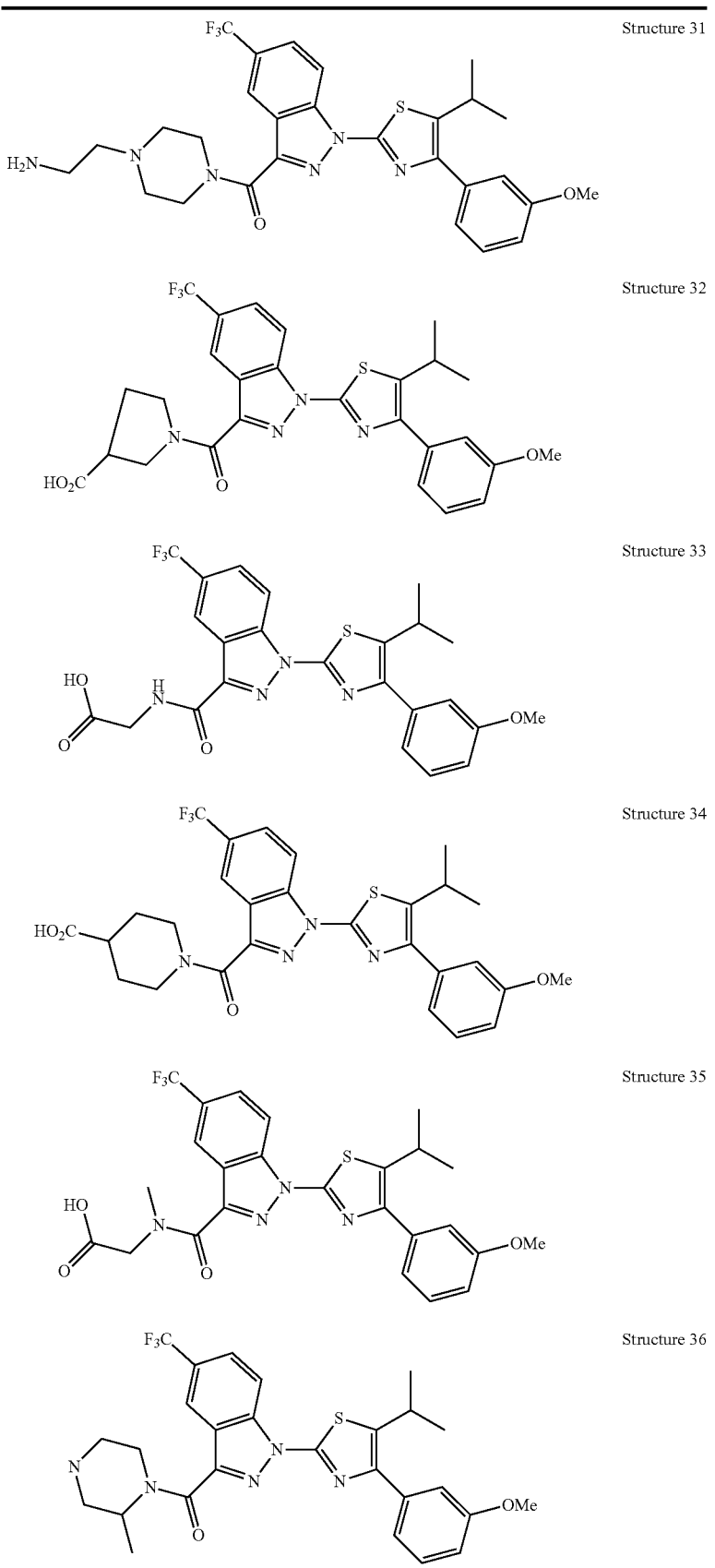
Structure 31
Structure 32
Structure 33
Structure 34
Structure 35
Structure 36

TABLE IV-continued
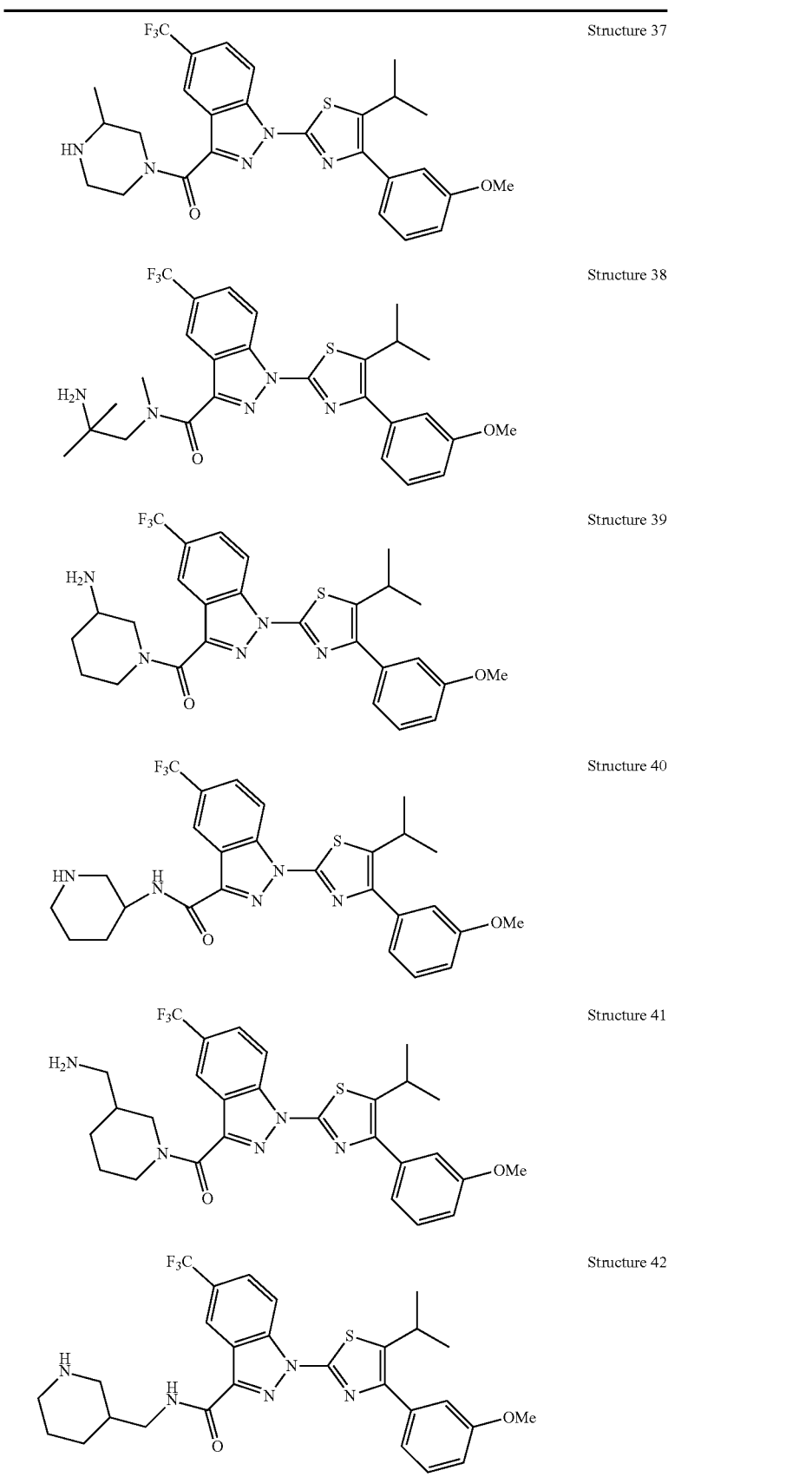

TABLE IV-continued
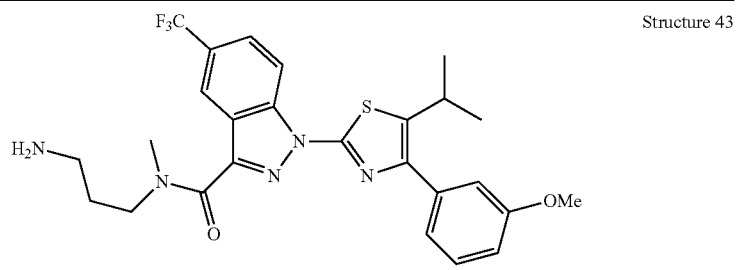
Structure 43
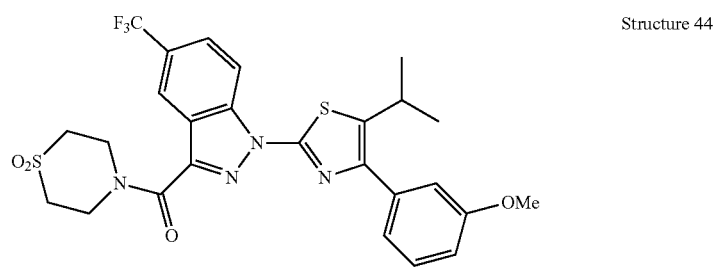
Structure 44
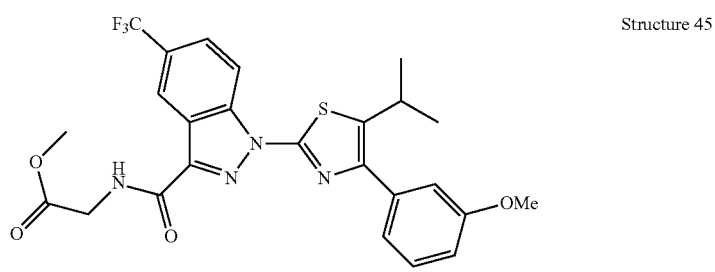
Structure 45
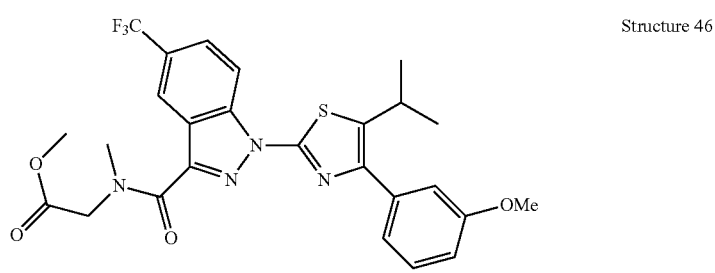
Structure 46
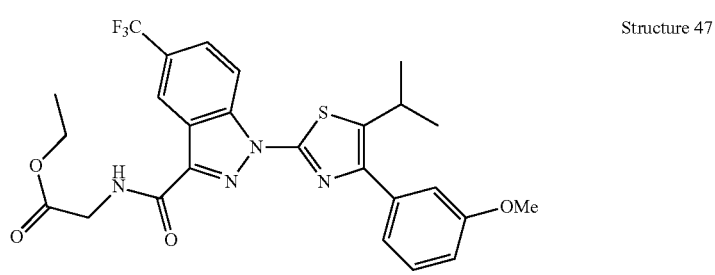
Structure 47
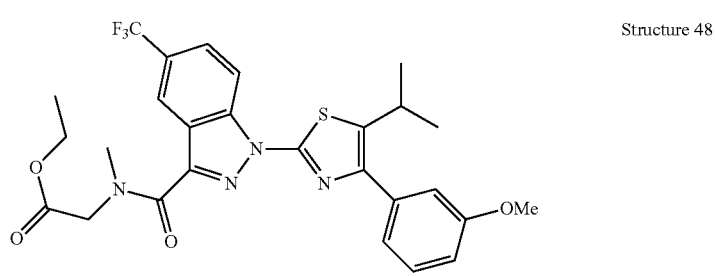
Structure 48

TABLE IV-continued
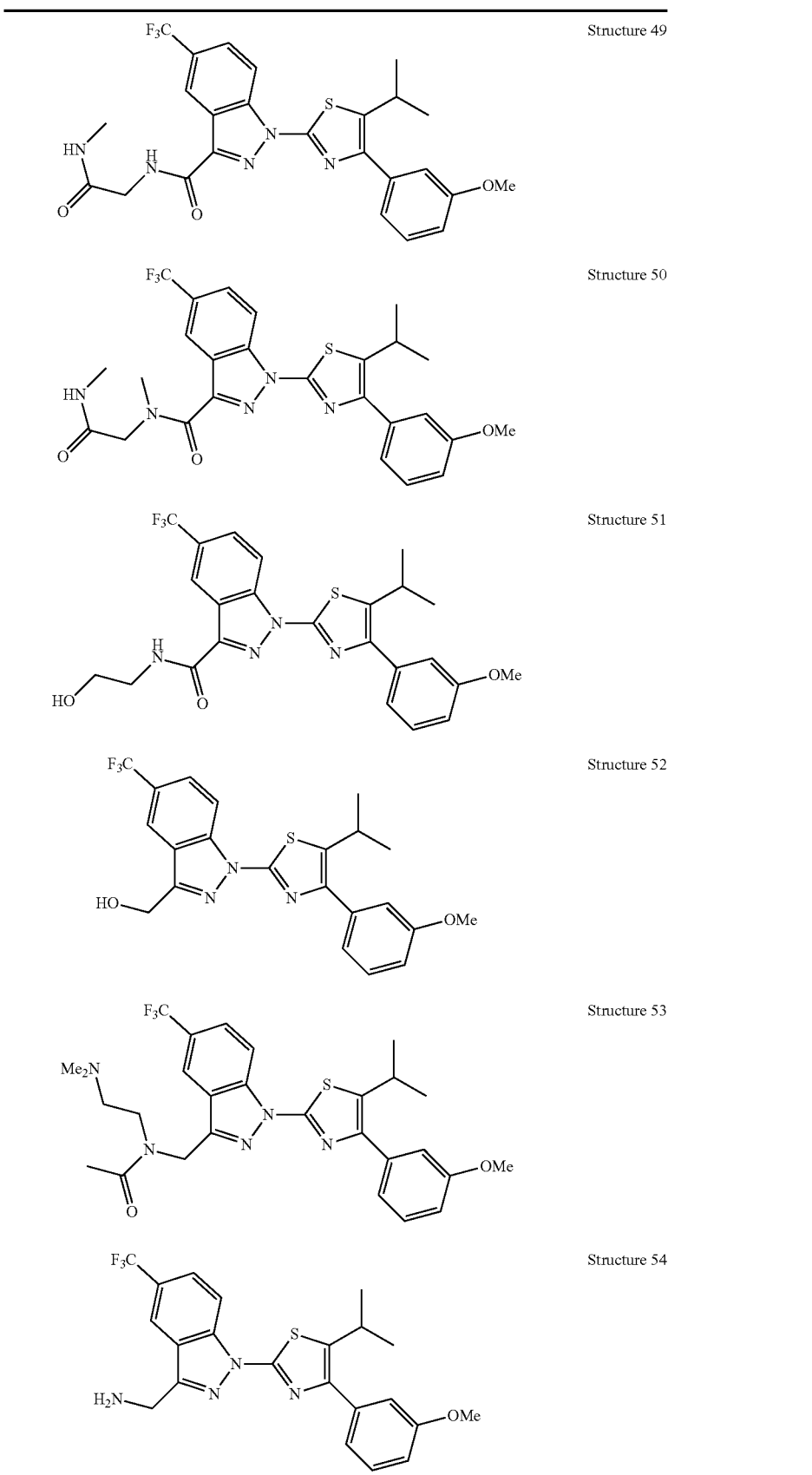
Structure 49
Structure 50
Structure 51
Structure 52
Structure 53
Structure 54

TABLE IV-continued
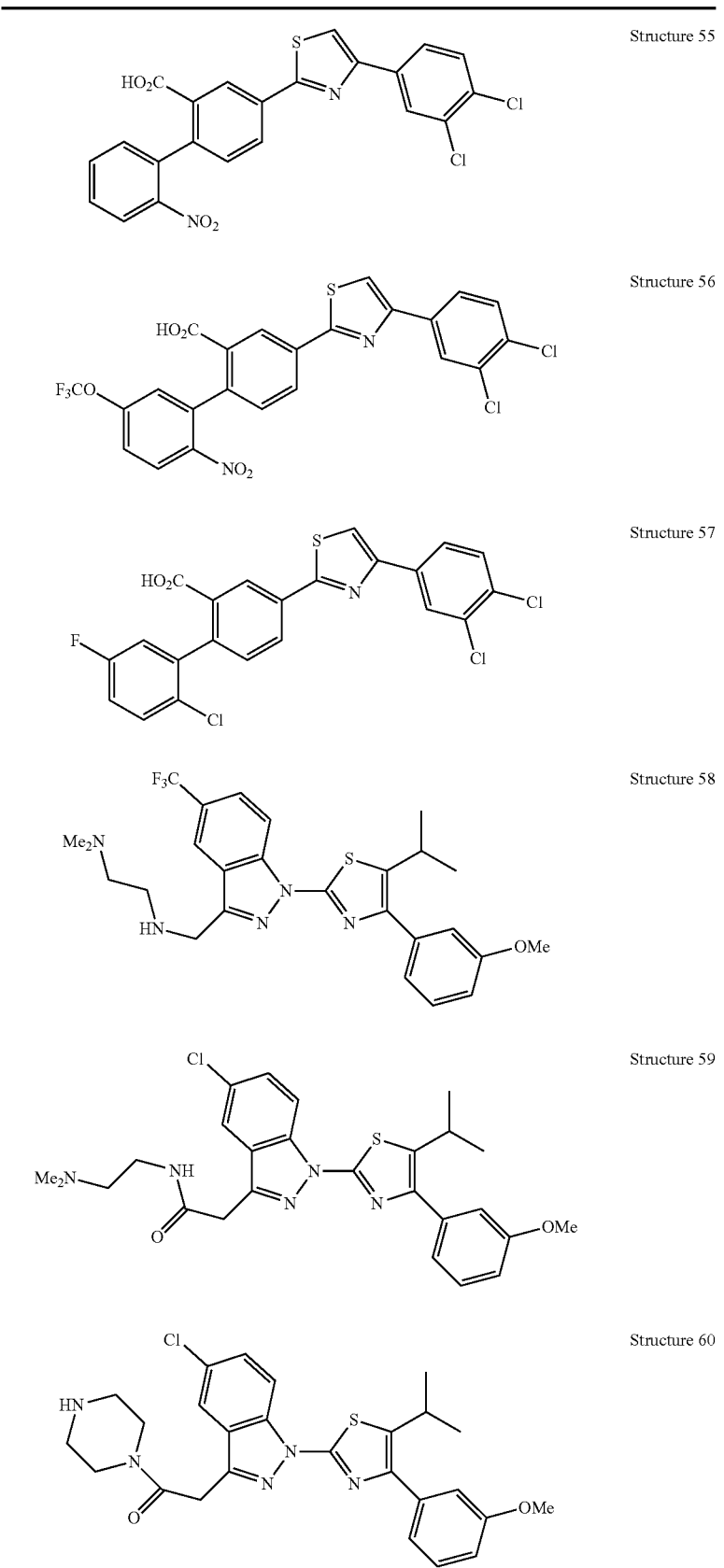
Structure 55
Structure 56
Structure 57
Structure 58
Structure 59
Structure 60

TABLE IV-continued

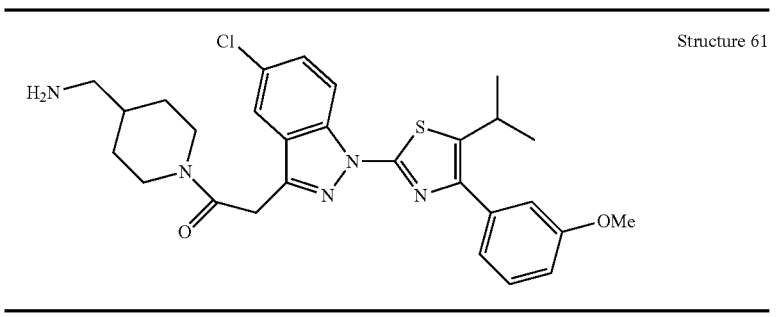

Structure 61

TABLE V

Properties of Structures

| # | Salt | Solid/Oil | AU-565 $EC_{50}$ (μM) | FP $EC_{50}$ (μM) | Cell viability in MDA-MB-453 breast | HeLa Cells FQ $IC_{50}$ (μM) | Compound Solubility DMSO | SBH cell AU565 (μM) |
|---|---|---|---|---|---|---|---|---|
| 4EGI-1Z | | | | good | 27.3 | 26.6 | | |
| 4EGI-1E | | | | good | 27.8 | 48.11 | | |
| 17 | | | 8.5-12.8 | | | | | |
| 2 | | | 9.1 | | | | | |
| 3 | | | 16-25 | | 40.18 | | | |
| 4 | | | | | 92.99 | | | |
| 5 | | | | | 57.65 | | | |
| 6 | | | | 13-20 | 93.32 | | | |
| 7 | | | | 9.8-14.7 | 295.76 | | | |
| 8 | | | | 18.00 | 321.82 | | | |
| 9 | | | | 24-36 | | | | |
| 10 | | | | 1.5 | 201.49 | | 1.2-1.7 | |
| 18 | n/a | light yellow powder | | | | | | |
| 19 | n/a | white powder | | | | | | |
| 20 | 0.2 formate salt | yellow powder | | | | | | |
| 21 | 0.2 formate salt | cream powder | | | | | | |
| 22 | n/a | yellow powder | | | | | | |
| 23 | 0.2 formate salt | cream solid | | | | | | |
| 24 | n/a | yellow powder | | | | | | |
| 25 | 0.2 formate salt | yellow powder | | | | | | |
| 26 | n/a | yellow powder | | | | | | |
| 27 | n/a | yellow powder | | | | | | |
| 28 | 0.7 formate salt | cream powder | | | | | | |
| 29 | 1.0 formate salt | cream powder | | | | | | |
| 30 | 0.8 formate salt | cream powder; 0.8 formate salt | | | | | | |
| 31 | 0.8 formate salt | cream powder | | | | | | |
| 32 | n/a | white solid | | | | | | |
| 33 | n/a | white solid | | | | | | |

TABLE V-continued

Properties of Structures

| # | Salt | Solid/Oil | AU-565 EC$_{50}$ (μM) | FP EC$_{50}$ (μM) | Cell viability in MDA-MB-453 breast | HeLa Cells FQ IC$_{50}$ (μM) | Compound Solubility DMSO | SBH cell AU565 (μM) |
|---|---|---|---|---|---|---|---|---|
| 34 | n/a | cream powder | | | | | | |
| 35 | n/a | cream powder | | | | | | |
| 36 | 0.5 formate salt | cream powder | | | | | | |
| 11 | 0.7 formate salt | cream powder | | | | | | 1.2-1.8 |
| 12 | 0.8 formate salt | cream solid | | | | | | 1.3-2.0 |
| 37 | 0.5 formate salt | cream solid | | | | | | |
| 38 | HCl | solid | | | | | | |
| 39 | HCl | solid | | | | | | |
| 40 | HCl | solid | | | | | | |
| 41 | HCl | solid | | | | | | |
| 42 | none | solid | | | | | | |
| 43 | HCl | solid | | | | | | |
| 13 | none | solid | | | 28.6 | | complete | 9-14 |
| 44 | none | solid | | | | | | |
| 45 | none | solid | | | 28.3 | | half/less | low |
| 46 | none | solid | | | | | little/no | 18-28 |
| 47 | none | solid | | | 28.7 | | complete | none |
| 48 | none | solid | | | 29.7 | | half/less | 12-18 |
| 49 | none | solid | | | | | half/less | low |
| 50 | none | solid | | | 31 | | half/less | 15-23 |
| 51 | none | gum | | | | | | |
| 52 | none | solid | | | | | | |
| 53 | none | gum | | | | | | |
| 54 | none | solid | | | | | | |
| 55 | | | | | 24.8 | | complete | 14-21 |
| 56 | | | | | 29.3 | | complete | 25-38 |
| 57 | | | | | | | little/no | 19-28 |
| 58 | | solid | | no activity | | | | |
| 14 | | solid | | very little | 28.9 | | complete | 21-31 |
| 59 | | solid | | no activity | | | | |
| 60 | | solid | | no activity | | | | |
| 61 | | solid | | No activity | | | | |
| 15 | | solid | | some | | | complete | 28-41 |
| 16 | | solid | | good | 27.5 | | complete | 5.3-8.0 |

While not wishing to be bound by theory, the putative mode of action of, for example, 4EGI-1 is to interfere with the interaction between eIF4E and eIF4G. As the compound of Formula I structurally mimics 4EGI-1, it is possible that the compound of Formula I binds to eIF4E and interferes with the interaction of eIF4E and eIF4G (either directly or indirectly), thereby preventing translation initiation.

Encompassed within the scope of the present disclosure is the design of additional small molecules based on the structure of Formulae I-IV. The substituted thiazole ring, for example, can be changed to one or more other heteroaryl or heterocyclic substituents. Selection of other heterocyclic substituents would be determined by the predicted structure-activity relationship (SAR) based on data from, for example, molecules conforming to the structure of Formulae I-IV.

Encompassed within the scope of the present disclosure is the design of, for example, structures of Formulae I-IV, wherein the structure comprises a heterocyclic or heteroaryl ring in place of the six-member aryl ring of the indazole. The ring can include, for example, N or S instead of the C depicted in the Indazole ring of Formulae I-IV.

One embodiment of the disclosure is directed to using one or more of the identified agents identified herein, identified through the use of a screen described herein or designed as described herein to treat a hyperproliferative disorder, e.g., cancer or a neurological disease or disorder. The compounds and formulations described herein can be delivered in a variety of ways and in doses appropriately determined by one of skill in the art.

"Treatment" refers to the administration of medicine or the performance of medical procedures with respect to a patient or subject, for either prophylaxis (prevention) or to cure or reduce the symptoms of the infirmity or malady in the instance where the patient is afflicted. Prevention of one or more hyperproliferative disorders, e.g., cancer, neurological disorders, e.g., Alzheimer's disease, or disorder(s) of the autism spectrum, e.g., autism, is included within the scope of treatment. The compounds described herein, identified through methods described herein or designed as described herein can be used as part of a treatment regimen in therapeutically effective amounts. A "therapeutically effective amount" is an amount sufficient to decrease, prevent or ameliorate the symptoms associated with a medical condition, or to effectively prevent or cure the medical condition. The present disclosure, for example, is directed to treatment using a therapeutically effective amount of a compound sufficient to treat one or more hyperproliferative disorders, e.g., cancer, neurological disorders, e.g., Alzheimer's disease, or disorder(s) of the autism spectrum, e.g., autism.

The terms "patient" and "subject" mean all mammals including humans.

The treatment(s) described herein are understood to utilize formulations including compounds identified herein, identified through methods described herein or designed as described herein and, for example, salts, solvates and co-crystals of the compound(s). The compounds of the present disclosure can exist in unsolvated as well as solvated forms with pharmaceutically acceptable solvents such as, for example, water, ethanol and the like. In general, the solvated forms are considered equivalent to the unsolvated forms for the purposes of the present disclosure.

The term "pharmaceutically acceptable salts, esters, amides and prodrugs" as used herein refers to those carboxylate salts, amino acid addition salts, esters, amides, prodrugs and inclusion complexes of the compounds of the present disclosure that are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the disclosure.

The term "prodrug" refers to compounds that are rapidly transformed in vivo to yield the parent compounds of the above formula, for example, by hydrolysis in blood (T. Higuchi and V. Stella, "Pro-drugs as Novel Delivery Systems," Vol. 14 of the A.C.S. Symposium Series; Bioreversible Carriers in Drug Design, ed. Edward B. Roche, American Pharmaceutical Association and Pergamon Press, 1987; both of which are incorporated herein by reference in their entirety). Activation in vivo may come about by chemical action or through the intermediacy of enzymes. Microflora in the GI tract may also contribute to activation in vivo.

The term "solvate" refers to a compound in the solid state, wherein molecules of a suitable solvent are incorporated. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions. Co-crystals are combinations of two or more distinct molecules arranged to create a unique crystal form whose physical properties are different from those of its pure constituents (Remenar, J. et al., *J. Am. Chem. Soc.*, 125:8456-7, 2003). Inclusion complexes are described in Remington: The Science and Practice of Pharmacy 19.sup.th Ed. (1995) volume 1, page 176-7. The most commonly employed inclusion complexes are those with cyclodextrins, and all cyclodextrin complexes, natural and synthetic, with or without added additives and polymer(s), as described in U.S. Pat. Nos. 5,324,718 and 5,472,954. The disclosures of Remenar, Remington and the '718 and '954 patents are incorporated herein by reference in their entireties.

The compounds can be presented as salts. The term "pharmaceutically acceptable salt" refers to salts whose counter ion derives from pharmaceutically acceptable non-toxic acids and bases. Suitable pharmaceutically acceptable base addition salts for the compounds of the present disclosure include, but are not limited to, metallic salts made from aluminum, calcium, lithium, magnesium, potassium, sodium and zinc or organic salts made from lysine, N,N-dialkyl amino acid derivatives (e.g., N,N-dimethylglycine, piperidine-1-acetic acid and morpholine-4-acetic acid), N,N'-dibenzylethylenediamine, chloroprocaine, choline, diethanolamine, ethylenediamine, meglumine (N-methylglucamine) and procaine. Where the compounds contain a basic residue, suitable pharmaceutically acceptable base addition salts for the compounds include, for example, inorganic acids and organic acids. Examples include acetate, benzenesulfonate (besylate), benzoate, bicarbonate, bisulfate, carbonate, camphorsulfonate, citrate, ethanesulfonate, fumarate, gluconate, glutamate, bromide, chloride, isethionate, lactate, maleate, malate, mandelate, methanesulfonate, mucate, nitrate, pamoate, pantothenate, phosphate, succinate, sulfate, tartrate, p-toluenesulfonate, and the like (Barge, S et al., 1977. *J. Pharm. Sci.*, 66:1-19, the entire contents of which are incorporated herein by reference).

Diluents that are suitable for use in the pharmaceutical composition of the present disclosure include, for example, pharmaceutically acceptable inert fillers such as microcrystalline cellulose, lactose, sucrose, fructose, glucose dextrose, or other sugars, dibasic calcium phosphate, calcium sulfate, cellulose, ethylcellulose, cellulose derivatives, kaolin, mannitol, lactitol, maltitol, xylitol, sorbitol, or other sugar alcohols, dry starch, saccharides, dextrin, maltodextrin or other polysaccharides, inositol or mixtures thereof. The diluent can be, for example, a water-soluble diluent. Examples of preferred diluents include, for example: microcrystalline cellulose such as Avicel PH112, Avicel PH101 and Avicel PH102 available from FMC Corporation; lactose such as lactose monohydrate, lactose anhydrous, and Pharmatose DCL 21; dibasic calcium phosphate such as Emcompress; mannitol; starch; sorbitol; sucrose; and glucose. Diluents are carefully selected to match the specific composition with attention paid to the compression properties. The diluent can be used in an amount of about 2% to about 80% by weight, about 20% to about 50% by weight, or about 25% by weight of the treatment formulation.

Other agents that can be used in the treatment formulation include, for example, a surfactant, dissolution agent and/or other solubilizing material. Surfactants that are suitable for use in the pharmaceutical composition of the present disclosure include, for example, sodium lauryl sulphate, polyethylene stearates, polyethylene sorbitan fatty acid esters, polyoxyethylene castor oil derivatives, polyoxyethylene alkyl ethers, benzyl benzoate, cetrimide, cetyl alcohol, docusate sodium, glyceryl monooleate, glyceryl monostearate, glyceryl palmitostearate, lecithin, medium chain triglycerides, monoethanolamine, oleic acid, poloxamers, polyvinyl alcohol and sorbitan fatty acid esters. Dissolution agents increase the dissolution rate of the active agent and function by increasing the solubility of the active agent. Suitable dissolution agents include, for example, organic acids such as citric acid, fumaric acid, tartaric acid, succinic acid, ascorbic acid, acetic acid, malic acid, glutaric acid and adipic acid, which may be used alone or in combination. These agents can also be combined with salts of the acids, e.g., sodium citrate with citric acid, to produce a buffer system. Other agents that can be used to alter the pH of the microenvironment on dissolution include salts of inorganic acids and magnesium hydroxide.

Disintegrants that are suitable for use in the pharmaceutical composition of the present disclosure include, for example, starches, sodium starch glycolate, crospovidone, croscarmellose, microcrystalline cellulose, low substituted hydroxypropyl cellulose, pectins, potassium methacrylate-divinylbenzene copolymer, poly(vinyl alcohol), thylamide, sodium bicarbonate, sodium carbonate, starch derivatives, dextrin, beta cyclodextrin, dextrin derivatives, magnesium oxide, clays, bentonite and mixtures thereof.

The active ingredient of the present disclosure can be mixed with excipients that are pharmaceutically acceptable and compatible with the active ingredient and in amounts suitable for use in the therapeutic methods described herein. Various excipients can be homogeneously mixed with the active agent of the present disclosure as would be known to those skilled in the art. The active agent, for example, can be mixed or combined with excipients such as but not limited to microcrystalline cellulose, colloidal silicon dioxide, lactose, starch, sorbitol, cyclodextrin and combinations of these.

Compositions of the present disclosure can also optionally include other therapeutic ingredients, anti-caking agents, preservatives, sweetening agents, colorants, flavors, desiccants, plasticizers, dyes and the like.

In certain embodiments, the compositions are administered in combination with a second therapeutic agent.

Any such optional ingredient must, of course, be compatible with the compound of the disclosure to insure the stability of the formulation. The dose range for adult humans is generally from 0.1 µg to 10 g/day orally. Tablets or other forms of presentation provided in discrete units can conveniently contain an amount of compound of the disclosure that is effective at such dosage or as a multiple of the same, for instance, units containing 0.1 mg to 500 mg, usually around 5 mg to 200 mg. The precise amount of compound administered to a patient will be the responsibility of the attendant physician. The dose employed will depend on a number of factors, including, for example, the age and sex of the patient, the precise disorder being treated, and its severity. The frequency of administration depends on the pharmacodynamics of the individual compound and the formulation of the dosage form, which is optimized by methods known in the art (e.g., controlled or extended release tablets, enteric coating etc.).

The compositions and methods described herein can be administered in conjunction with assays to determine whether a subject is sensitive to treatment. A subpopulation of, for example, cancer patients, Alzheimer's patients or autism patients may be sensitive to one or more inhibitors of eIF4E, as described herein, whereas other subpopulation(s) may be resistant or remain unaffected by eIF4E inhibitors. Treatment sensitivity can be determined, for example, by blood tests, genetic screening, RNA profiling, etc.

In certain embodiments, the compounds disclosed herein are optionally substituted with one or more substituents. The term "substituted" refers to a molecule wherein at least one hydrogen atom is replaced with a substituent. When substituted, one or more of the groups are "substituents." The molecule can be multiply substituted. In the case of an oxo substituent ("=O"), two hydrogen atoms are replaced. Example substituents within this context include, for example, halogen, hydroxy, alkyl, alkoxy, alkanoyl, nitro, cyano, oxo, carbocyclyl, carbocycloalkyl, heterocarbocyclyl, heterocarbocycloalkyl, aryl, arylalkyl, heterocarbocyclyl, heteroaryl, heteroarylalkyl, —NRaRb, —NRaC(=O)Rb, —NRaC(=O)NRaNRb, —NRaC(=O)ORb, —NRaSO2Rb, —C(=O)Ra, —C(=O)ORa, —C(=O)NRaRb, —OC(=O)NRaRb, —ORa, —SRa, —SORa, —S(=O)2Ra, —OS(=O)2Ra and —S(=O)2ORa. Ra and Rb in this context may be the same or different and independently hydrogen, halogen, hydroxyl, alkyl, alkoxy, alkanoyl, amino, alkylamino, dialkylamino, alkylthiol, carbocyclyl, carbocycloalkyl, heterocarbocyclyl, heterocarbocycloalkyl, aryl, arylalkyl, heteroaryl, heteroarylalkyl. The term "optionally substituted," as used herein, means that substitution is optional and therefore it is possible for the designated atom or compound is unsubstituted.

As used herein, "alkyl" means a noncyclic straight chain or branched, unsaturated or saturated hydrocarbon such as those containing from 1 to 10 carbon atoms, while the term "lower alkyl" or "$C_{1-6}$ alkyl" has the same meaning as alkyl but contains from 1 to 6 carbon atoms. The term "higher alkyl" has the same meaning as alkyl but contains from 7 to 10 carbon atoms. Representative saturated straight chain alkyls include, for example, methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl," respectively). Representative straight chain and branched alkenyls include, for example, ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl and the like.

As used herein, "haloalkyl" refers to halo-substituted alkyl groups.

Non-aromatic mono or polycyclic alkyls are referred to herein as "carbocycles" or "carbocyclyl" or "cyclic alkyl" groups. Representative saturated carbocycles include, for example, cyclopropyl, cyclobutyl, cyclopentyl, cyclohexyl, and the like; while unsaturated carbocycles include, for example, cyclopentenyl and cyclohexenyl, aryls and the like.

"Heterocarbocycles" or "heterocarbocyclyl" groups are carbocycles that contain from one to four heteroatoms independently selected from, for example, nitrogen, oxygen and sulfur (which may be saturated or unsaturated (but not aromatic)), monocyclic or polycyclic, and wherein the nitrogen and sulfur heteroatoms can be optionally oxidized, and the nitrogen heteroatom can be optionally quaternized. Heterocarbocycles include, for example, morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl.

As used herein, "heteroaryl" refers an aromatic heterocarbocycle having one to four heteroatoms selected from, for example, nitrogen, oxygen and sulfur, and containing at least one carbon atom, including both mono- and polycyclic ring systems. Polycyclic ring systems can, but are not required to, contain one or more non-aromatic rings, as long as one of the rings is aromatic. Representative heteroaryls are, for example, furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes, for example, N-alkylated derivatives such as a 1-methylimidazol-5-yl substituent.

As used herein, "heterocycle" or "heterocyclyl" refers to mono- and polycyclic ring systems having one to four heteroatoms selected from, for example, nitrogen, oxygen and sulfur, and containing at least one carbon atom. The mono- and polycyclic ring systems can be aromatic, non-aromatic or mixtures of aromatic and non-aromatic rings. Heterocycle includes heterocarbocycles, heteroaryls, and the like.

"Alkoxy" refers to an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy.

"Alkylamino" refers an alkyl group as defined above with the indicated number of carbon atoms attached through an amino bridge. An example of an alkylamino is methylamino, (e.g., —NH—$CH_3$).

"Alkanoyl" refers to an alkyl as defined above with the indicated number of carbon atoms attached through a carbonyl bridge (i.e., —(C=O)alkyl).

The compounds of this disclosure can exist in radiolabeled form, i.e., the compounds can contain one or more atoms containing an atomic mass or mass number different from the atomic mass or mass number most commonly found in nature. Radioisotopes of, for example, hydrogen, carbon, phosphorous, fluorine, and chlorine include $^2$H, $^3$H, $^{13}$C, $^{14}$C, $^{15}$N, $^{35}$S, $^{18}$F and $^{36}$Cl, respectively. Compounds that contain those radioisotopes and/or other radioisotopes of other atoms are within the scope of this disclosure. Radiolabeled compounds of the present disclosure and prodrugs thereof can generally be prepared by methods well known to those skilled in the art.

The compounds described herein can contain asymmetric centers and can thus give rise to enantiomers, diastereomers and other stereoisomeric forms. Each chiral center can be defined in terms of absolute stereochemistry as (R)- or (S)-. The present disclosure is meant to include all such possible isomers, as well as, their racemic and optically pure forms. Optically active (R)- and (S)-isomers can be prepared using chiral synthons or chiral reagents, or resolved using conventional techniques. The representation of the configuration of any carbon-carbon double bond appearing herein is selected for convenience only, and unless explicitly stated, is not intended to designate a particular configuration. Thus a carbon-carbon double bond depicted arbitrarily as E can be Z, E, or a mixture of the two in any proportion. Likewise, all tautomeric forms are also intended to be included.

The formulations include those suitable for oral, parenteral (including subcutaneous, intradermal, intramuscular, intravenous and intraarticular), rectal and topical (including dermal, buccal, sublingual and intraocular) administration. The most suitable route depends upon the condition and disorder of the recipient. The formulations can conveniently be presented in unit dosage form and can be prepared by any of the methods known in the art of pharmacy. All methods include the step of bringing into association at least one compound of the present disclosure or a pharmaceutically acceptable salt or solvate thereof ("active ingredient") with the carrier, which constitutes one or more accessory ingredients. In general, the formulations are prepared by uniformly and intimately bringing into association the active ingredient with liquid carriers or finely divided solid carriers or both and then, if necessary, shaping the product into the desired formulation.

The pharmaceutical preparations of the disclosure are preferably in a unit dosage form, and can be suitably packaged, for example in a box, blister, vial, bottle, sachet, ampoule or in any other suitable single-dose or multi-dose holder or container (which may be properly labeled); optionally with one or more leaflets containing product information and/or instructions for use. Such unit dosages generally contain between 1 and 1000 mg, and usually between 5 and 500 mg, of the at least one compound of the disclosure, e.g., about 10, 25, 50, 100, 200, 300 or 400 mg per unit dosage.

Formulations of the present disclosure suitable for oral administration can be presented as discrete units such as capsules, cachets or tablets each containing a predetermined amount of the active ingredient; as a powder (including micronized and nanoparticulate powders) or granules; as a solution or a suspension in an aqueous liquid or a non-aqueous liquid; or as an oil-in-water liquid emulsion or a water-in-oil liquid emulsion. The active ingredient can also be presented as a bolus, electuary or paste.

A tablet can be made by compression or molding, optionally with one or more accessory ingredients. Compressed tablets can be prepared by compressing in a suitable machine the active ingredient in a free-flowing form such as a powder or granules, optionally mixed with a binder, lubricant, inert diluent, lubricating, surface active or dispersing agent. Molded tablets can be made by molding in a suitable machine a mixture of the powdered compound moistened with an inert liquid diluent. The tablets can optionally be coated or scored and can be formulated so as to provide sustained, delayed or controlled release of the active ingredient therein.

The treatments (therapies) described herein can also be part of "combination therapies." Combination therapy can be achieved by administering two or more agents, each of which is formulated and administered separately, or by administering two or more agents in a single formulation. The second active ingredient can be, for example, a second compound identified herein or through screens described herein, designed as described herein or active ingredients, for example, mTOR inhibitors or Her2 antagonists (e.g., Trastuzumab)(Zindy, P. et al., *Cancer Res.*, 71:4068-73, 2011), thalidomide or thalidomide derivatives (Li, S. et al., *Blood*, 117:5157-65, 2011) useful for treating, for example, a hyperproliferative disorder, e.g., cancer, a neurological disorder, e.g., Alzheimer's disease, or a disorder from the autism spectrum, e.g., autism, symptoms associated with the disease or disorder, or symptoms associated with treatment by the first active agent ("side effects"). In particular, the methods and compositions described herein can be used in combination with one or more therapeutics agents that act synergistically with modulation of eIF4E or CAP-dependent translation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within any number of hours of each other or within any number or days or weeks of each other.

The present disclosure is also directed to kits for treating or preventing one or more hyperproliferative disorders, e.g., cancer, a neurological disorder, e.g., Alzheimer's disease, or a disorder from the autism spectrum, e.g., autism, comprising compound(s) identified herein, compound(s) identified through the screening methods provided herein, or compounds designed as described herein. The kits of the present disclosure can include, for example, components necessary for delivering a therapeutically effective amount of the active agent, instructions for use and/or devices for delivery of the active agent(s).

The present disclosure is also directed to models and screening methods useful for identifying molecules that modulate eIF4E activity and demonstrate cytotoxic effects. Compounds as identified can be used in the methods, formulations and kits described herein. The compounds identified herein can be validated for their efficacy in treating one or more hyperproliferative disorders, e.g., cancer, a neurological disorder, e.g., Alzheimer's disease, or a disorder from the autism spectrum, e.g., autism, for example, by using cellular, animal and/or human models. Briefly, a candidate test compound, which can include a compound designed as described herein or a compound with the structure of Formula I, is assayed for its cytotoxic activity and/or its ability to bind eIF4E and/or its ability to disrupt the interaction of eIF4E and eIF4G.

EXEMPLIFICATION

Example 1

Synthesis of Compounds

FIGS. 1-4 show synthesis pathways for generating various compounds described herein.

Figure 1B:
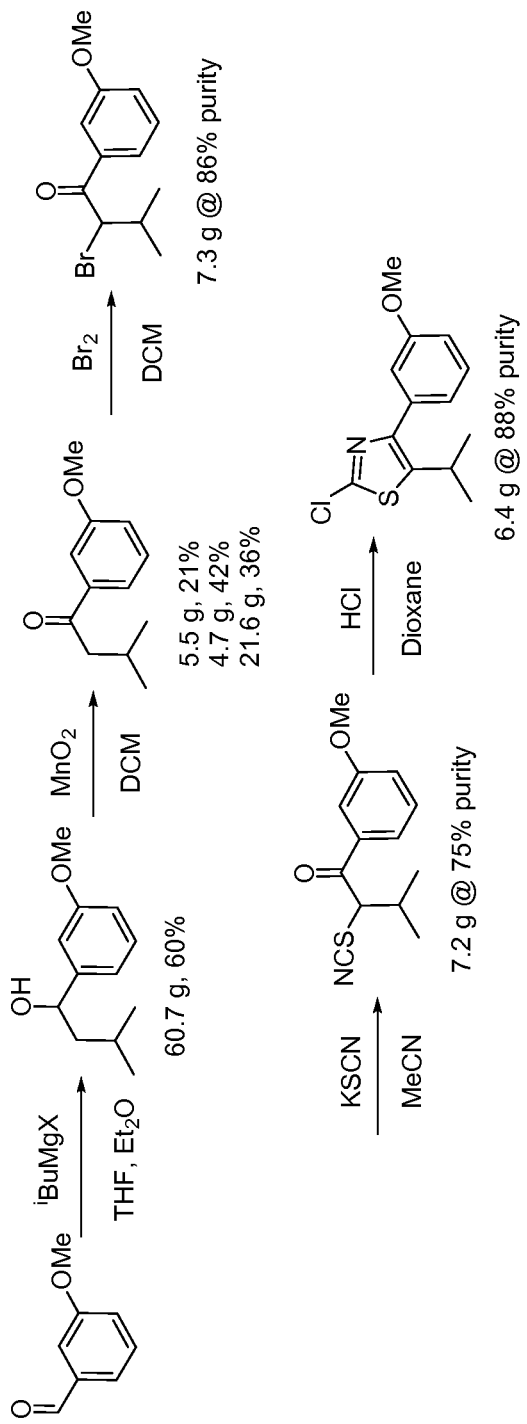
Figure 1C:
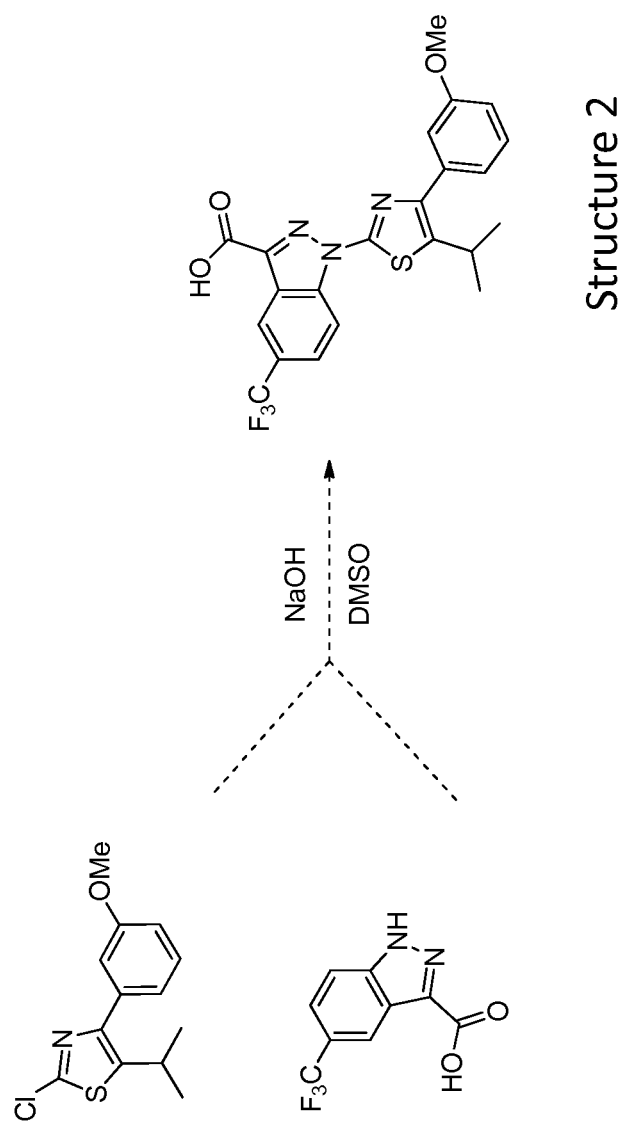

FIGS. 1A-C show various stages during the synthesis of Structure 2. The synthesis of the indazole acid (FIG. 1A) proceeded batch-wise from the Boc-aniline. The glyoxylic acid was obtained at 70-85% purity and progressed without purification. Cyclisation to the isatin was achieved by heating an acidic solution of the glyoxylic acid. The isatin was purified by trituration from 1:2, Et$_2$O:isohexane and all three batches were obtained at >95% purity. Following a successful small scale trial conversion of the isatin to the indazole acid the material was progressed in 3 batches to afford a total of 26.7 g of indazole acid at 80% purity.

The synthesis of the chlorothiazole group was taxing, as difficulties were encountered during the oxidation reaction, despite using a large excess of activated MnO$_2$ prolonged reaction times were required and poor yields of the ketone obtained. A 5 g batch of the ketone was converted to the chlorothiazole.

For the final stage synthesis (FIG. 1C), a 1 g trial SNAr reaction is used to check that the indazole acid at this purity reacts as expected. This reaction proceeded slowly with 37% conversion by LCMS after 3 days.

Figure 2:
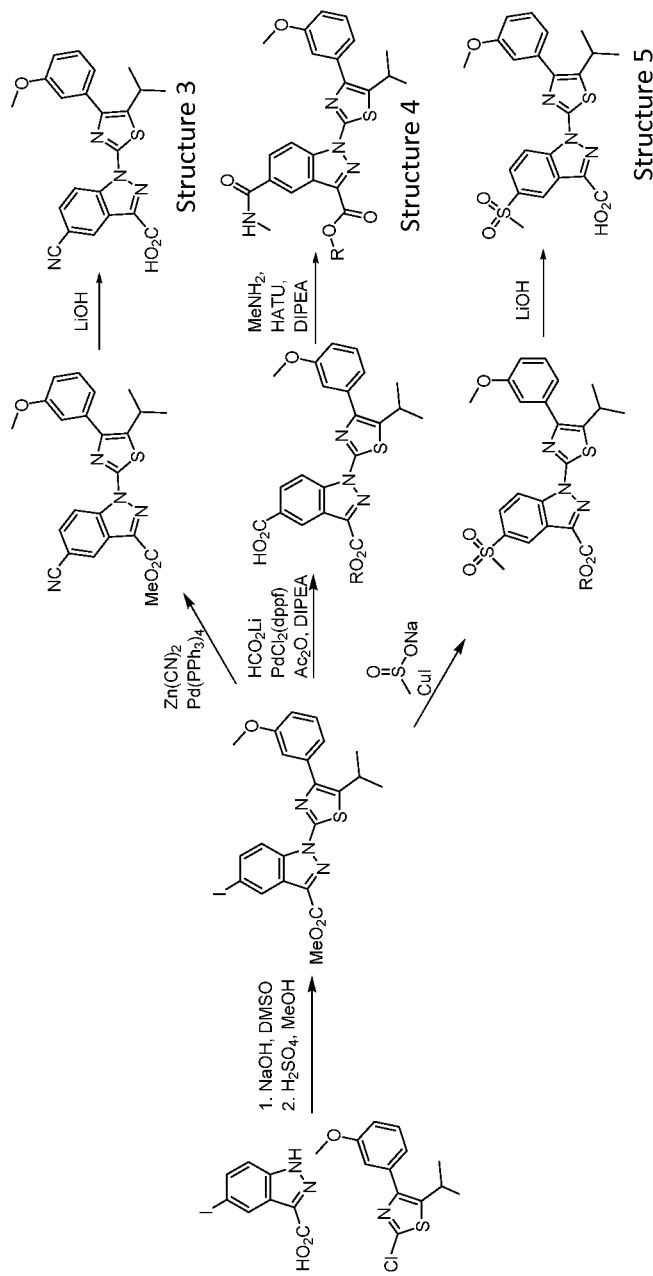
FIG. 2 is a schematic representation of the synthesis pathway for Structure 3, Structure 4 and Structure 5.

FIG. 2 shows the synthesis for the Structure 3 series of structures. From the required iodo intermediate cyanation afforded the nitrile in good yield and subsequent hydrolysis gave target Structure 3. Carbonylation and hydrolysis afforded target Structure 4 in good yield over the two steps. Formation of the sulfone was achieved through displacement with sodium methane sulfinate in the presence of CuI and target Structure 5 was isolated following ester hydrolysis.

Figure 3:
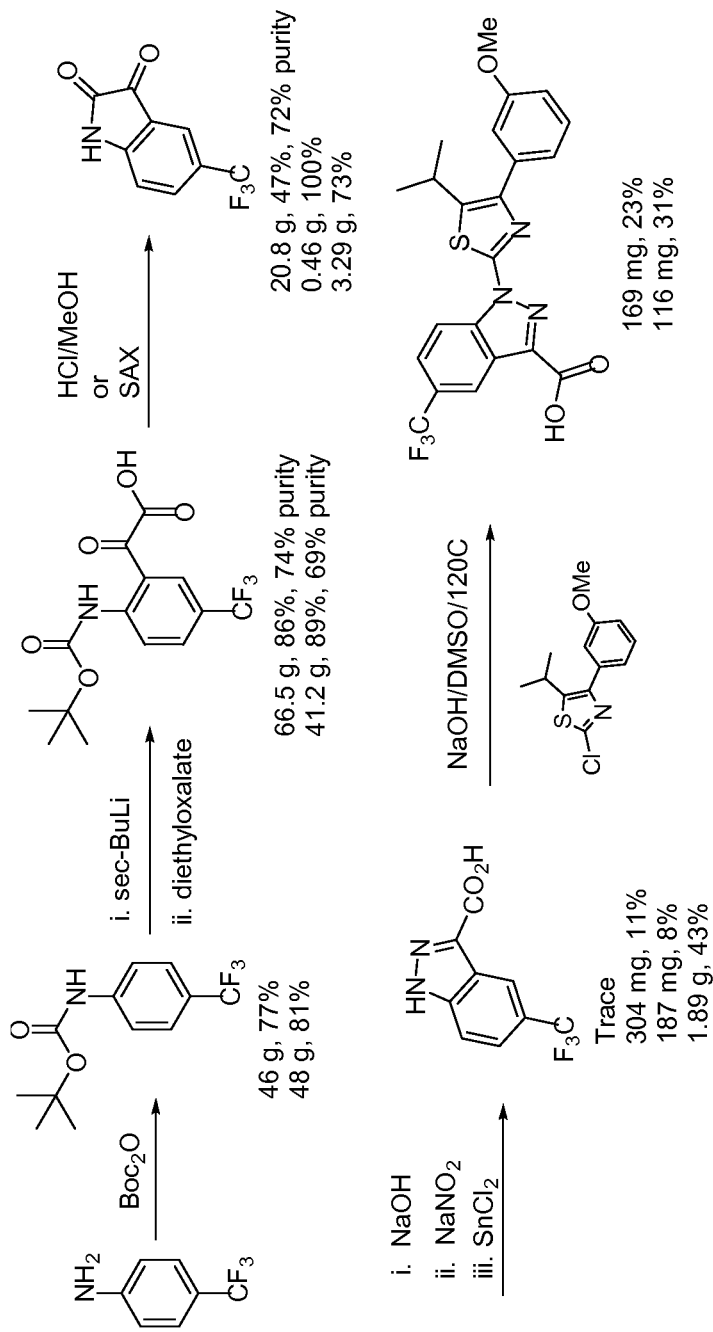
FIG. 3 is a schematic representation of the synthesis pathway for a molecule that is a precursor for the Structure 6 series of structures.
Figure 4:
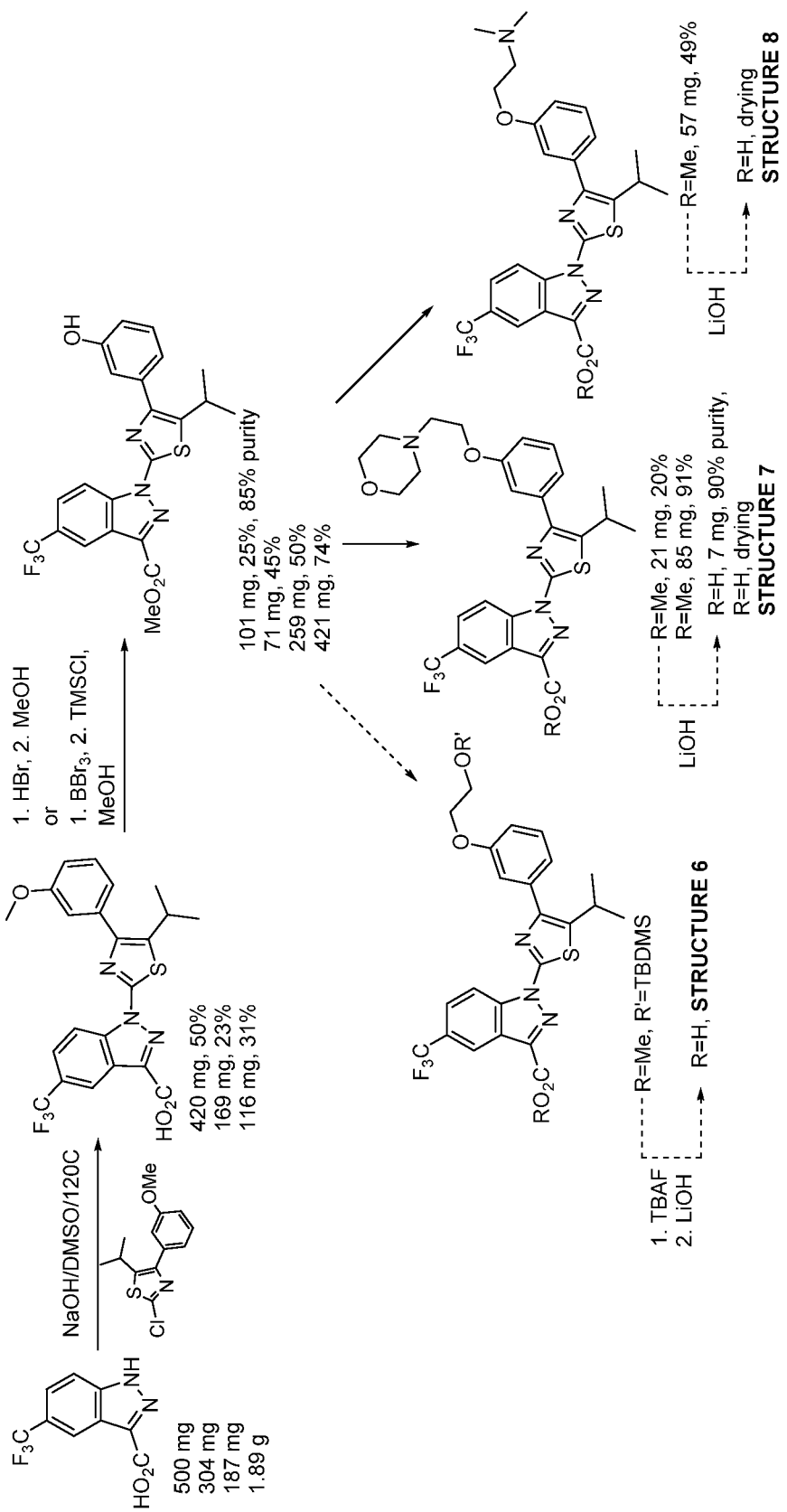
FIG. 4 is a schematic representation of the synthesis pathway for Structure 6, Structure 7 and Structure 8.

FIG. 3 shows the synthesis of some of the Structure 6 series of structures. On first attempting this synthesis, lithiation and quenching with diethyloxalate resulted in formation of the pyruvic acid rather than the pyruvate. This material was progressed to the isatin and purification attempted at this stage, rather unsuccessfully. Progression of the impure isatin resulted in only trace amounts of the required indazole. The synthesis was repeated and a modified work-up employed (quenching the reaction with EtOH) in an effort to isolate the pyruvate, but still the acid was obtained. Purification of the acid using capture and release on SAX was successful in both purification and effecting cyclisation to the isatin. Progression of this batch of pure isatin gave a much improved yield of the indazole.

Figure 5:
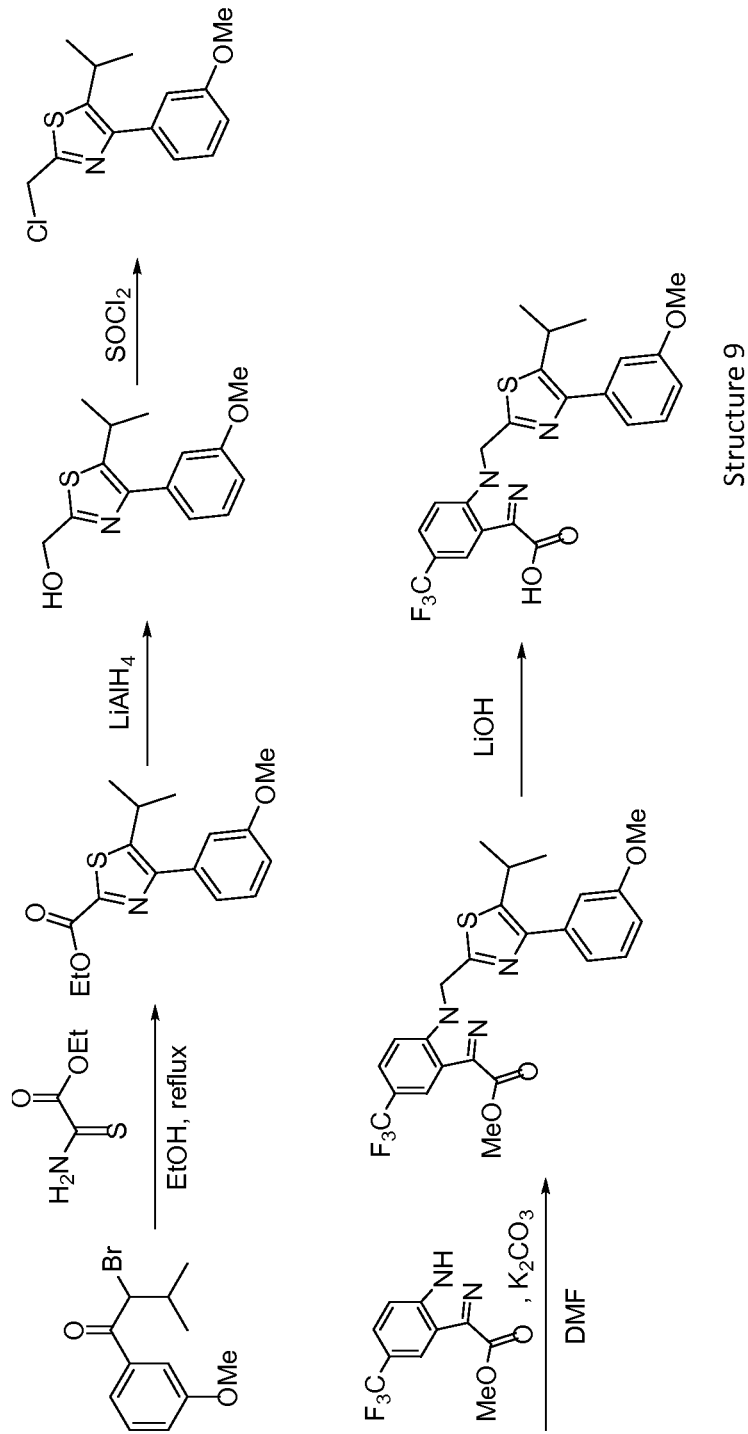
FIG. 5 is a schematic representation of the synthesis pathway for Structure 9.

FIG. 5 shows the synthesis of specific Structure 6 compounds. The two step procedure using BBr$_3$ for the deprotection and isolation of the phenol acid intermediate prior to esterification was investigated on a small scale with much improved results. The process was successfully scaled up to afford a further ~650 mg of material. The alkylations with chloroethylmorpholine and chloroethyldimethylamine proceeded well as did the subsequent hydrolysis reactions. Both materials have been purified. Alkylation with bromoethanol was unsuccessful (the reaction stalled at ~20%), but using TBDMS-protected bromoethanol was successful.

Figure 6:
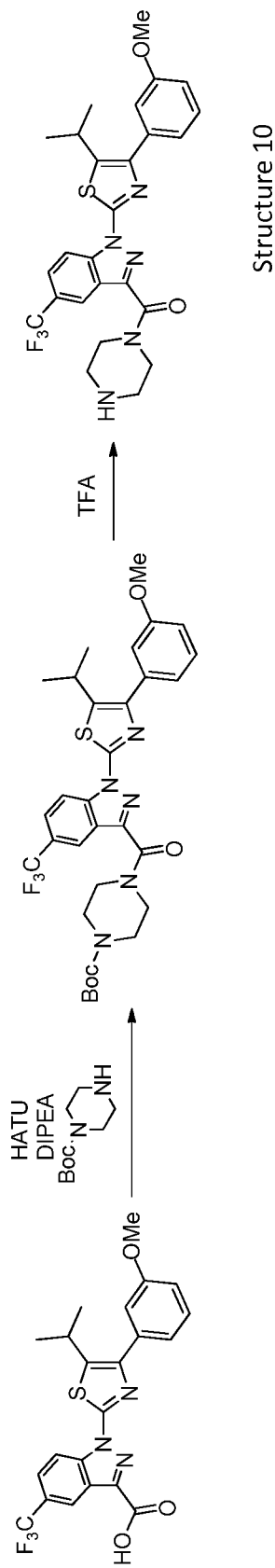
FIG. 6 is a schematic representation of the synthesis pathway for Structure 10.

FIG. 6 shows the synthesis of Structure 9. Cyclisation to thiazole proceeded very slowly; the reaction was stopped after 7 days to afford 21% of the intermediate. Ester reduction and chlorination of the alcohol proceeded well as did the subsequent indazole alkylation. Ester hydrolysis afforded the target in good yield.

Figure 7:
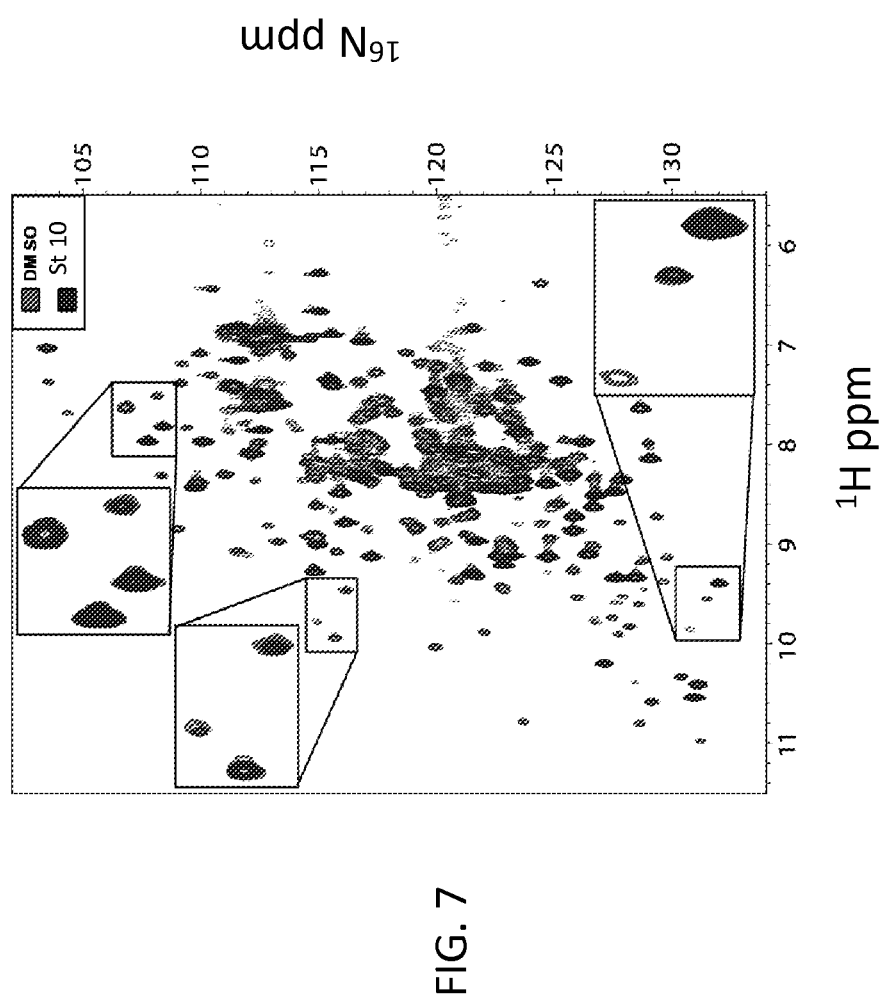
FIG. 7 is a plot showing NMR data demonstrating binding of Structure 10 to eIF4E.

FIG. 7 shows the synthesis of Structure 10. The acid was progressed to amide in good yield. Subsequent Boc-deprotection with TFA afforded the target, Structure 10 as the hydrochloride salt.

Example 2

Fluorescence Polarization Assay/Demonstration of Binding by NMR

Binding of a compound described herein, Structure 10, to eIF4E was demonstrated by NMR (FIG. 7). The effect of the bound compound on the activity of eIF4e was further addressed using a Fluorescence Polarization (FP) assay. The FP assay was used to monitor the eIF4E/eIF4G interaction. The eIF4E/eIF4G complex was exposed to Structure 10, and the dissociation of eIF4G from eIF4E was measured using the FP assay.

FP Assay Materials 18 amino acid FITC-labeled 4G peptide (Moerke, N. et al., *Cell*, 128:257-67, 2007).
Recombinant eIF4E
FP buffer
Compounds as 12.5 mM solutions in DMSO A master mixture of 20 nM peptide, 400 µM recombinant 4EGI-1 in NMR buffer was made. 240 µL of this master mix was transferred to a separate tube and 3.2 µL of DMSO was added. 30 µL aliquots of this mixture was then added to each of six wells of 384-well black plate. These are the maximum polarization wells. The minimum polarization wells were determined using peptide only at a concentration of 20 nM. The experimental wells were created by adding 3.2 µL of each 12.5 mM solution of a test compound to the master mixture. The compound mixtures were serially diluted to create a six point dose response curve (with six different concentrations of each test compound).

The control and experimental mixtures were incubated for 30 minutes and then read in a fluorescent micro-plate capable of measuring fluorescent polarization. The triplicate averages of the readings were determined. The difference between the maximum and minimum values yielded net polarization, which is considered full signal of the assay (100% control).

The activity of compound at each concentration was determined by comparing the FP signal in the presence of compound to the control (no compound) value. The percent inhibition is =100–((FP compound/FP control)×100).

Figure 8:
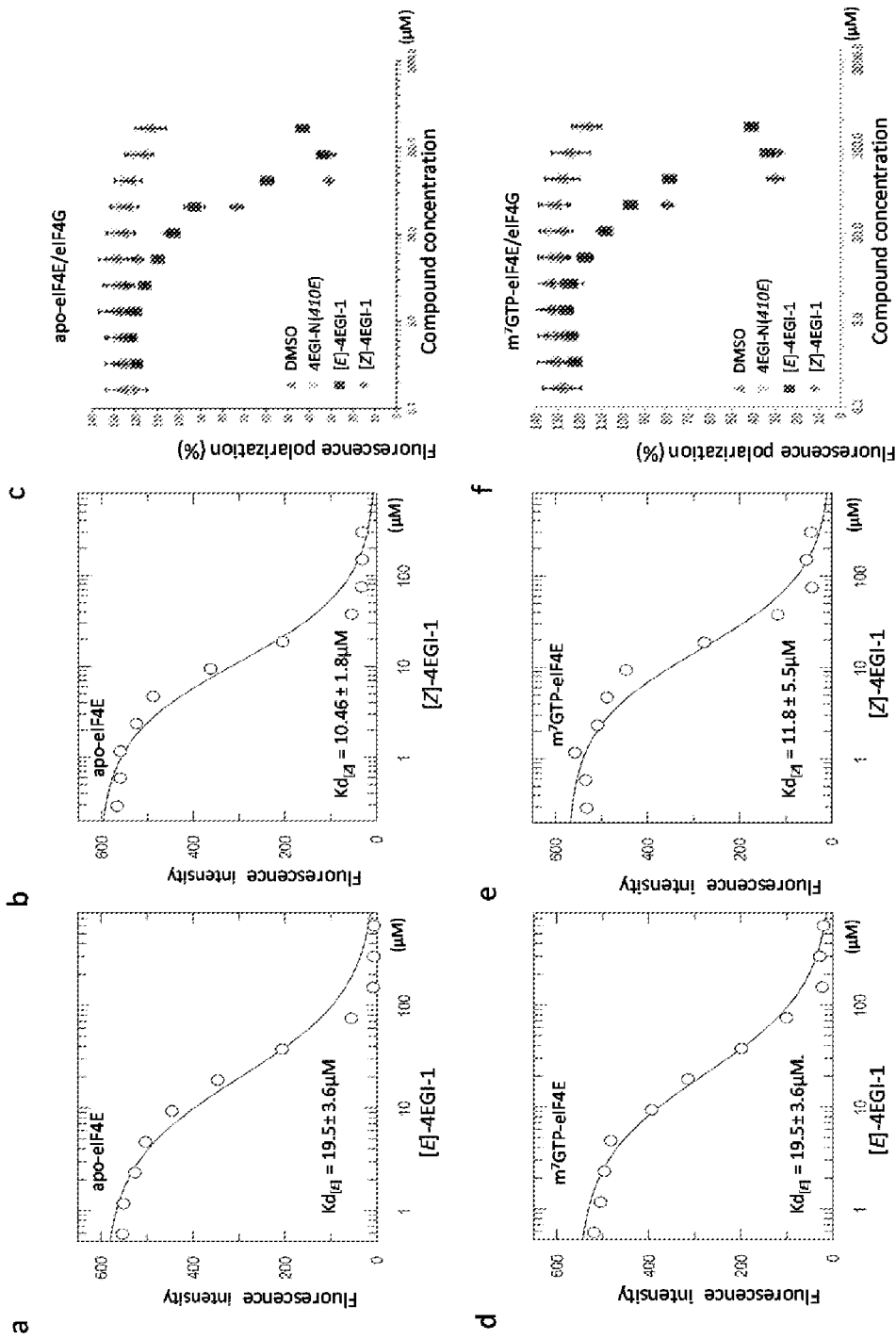
FIG. 8 is a series of plots showing data from fluorescence polarization (FP) assays. The plots show the efficacy of a known eIF4E inhibitor, 4EGI-1, thereby validating the assay as a way to measure dissociation of eIF4G from eIF4E (see Example 2).

Results showing the use of this assay for a known eIF4E inhibitor, 4EGI-1, are shown in FIG. 8.

Example 3

Fluorescence Quenching Assay

Figure 9:
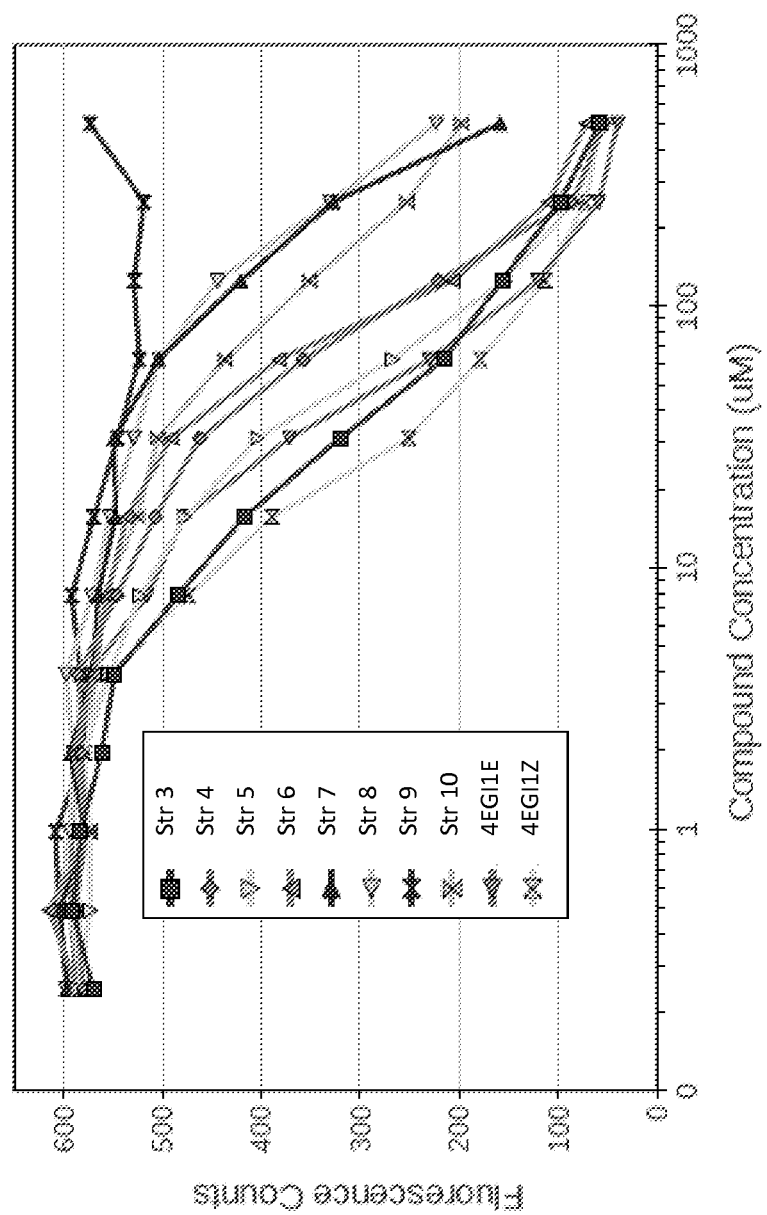
FIG. 9 shows the effect of various test compounds on tryptophan quenching, indicating binding to eIF4E (see EXAMPLE 3).

Exposed tryptophan side chains are measured in a spectrometer. Tryptophan, when excited at 280 nm, emits light at 350 nm. The degree to which tryptophan emissions are quenched is a measure of binding of a test compound to eIF4E, as tryptophan side chains become "buried" upon compound binding. FIG. 9 shows the results of measuring tryptophan quenching with various compounds described herein at various concentrations.

Example 4

"In Cell" HeLa Cell Luciferase Assay

Figure 10:
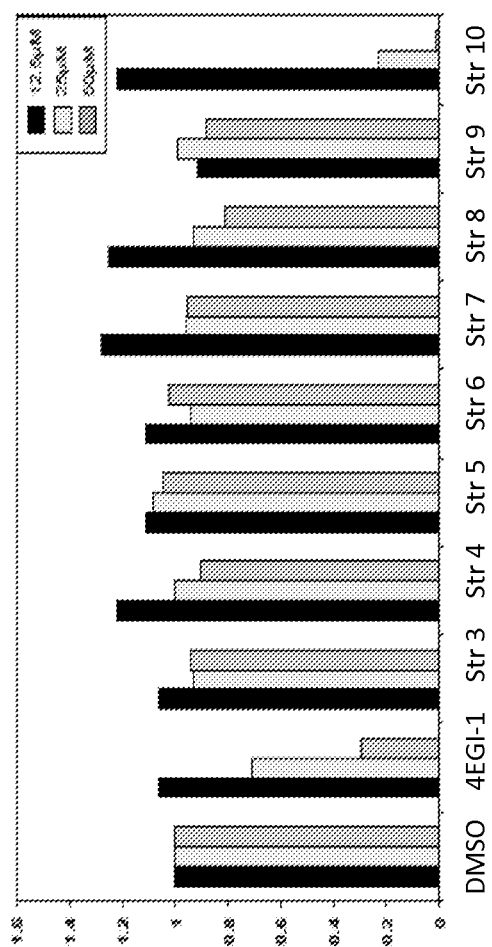
FIG. 10 is a bar plot of data showing the effect of various test compounds on translation initiation (see EXAMPLE 4).

HeLa cells were transfected with a bicistronic dual luciferase construct (2×EMCV Luc Plasmid-firefly and EMCV IRES dependent *Renilla* luciferase). One reporter construct was CAP-dependent, and the other was not. The cells were treated with DMSO in the presence or absence of various compounds described herein for 10 hours (compounds shown are in 50 μM serial dilutions). Cells were evaluated for Luc activity according to the Promega Dual Glo manufacturer instructions. Results are shown in FIG. 10.

Example 5

Polysome Profile

Materials
Cells, plated in 140 mm culture dishes; in mid log phase of growth (4-5 plates per treatment.
Test compounds as 40 mM master solutions in DMSO
Lysis buffer: 15 mM Tris pH 7.4, 15 mM $MgCl_2$, 150 mM NaCl, 1% TritonX-100, 100 μg/mL cycloheximide, 1 mg/mL Heparin.
Polysome buffer: 15 mM Tris pH7.4, 15 mM $MgCl_2$, 150 mM NaCl, 100 μg/mL cycloheximide.
1. Cells were incubated with the desired concentrations of each compound for 2 hours.
2. Cells were incubated with 100 μg/mL cycloheximide in media for 5 min at 37 C, after which the media was removed from the late, and the plate was put on ice.
3. Cells were washed twice with 5 mL PBS+100 μg/mL CHX.
4. Cells were harvested, resuspended in 375 μl of LSB with 1 mM DTT and 100 U/mL RNAsin.
5. 125 μL of lysis buffer was added, and the cells were subjected to 10 strokes in a homgenizer.
6. The lysed cells were spun to remove cellular debris, and the supernatant was transferred to fresh tubes.
7. 15 μL of 5M NaCl and 50 μL of 10 mg/mL Heparin was added. A 20 μL aliquot was taken and stored. The remainder of the supernatant mixture was taken to a volume of 1 mL and the $OD_{260/280}$ was read.
8. Aliquots of the supernatant mixture were then applied to a 15-50% sucrose gradient and spun for 105 minutes. The sucrose gradient was then fractionated and the $OD_{254}$ was measured.

Figure 11:
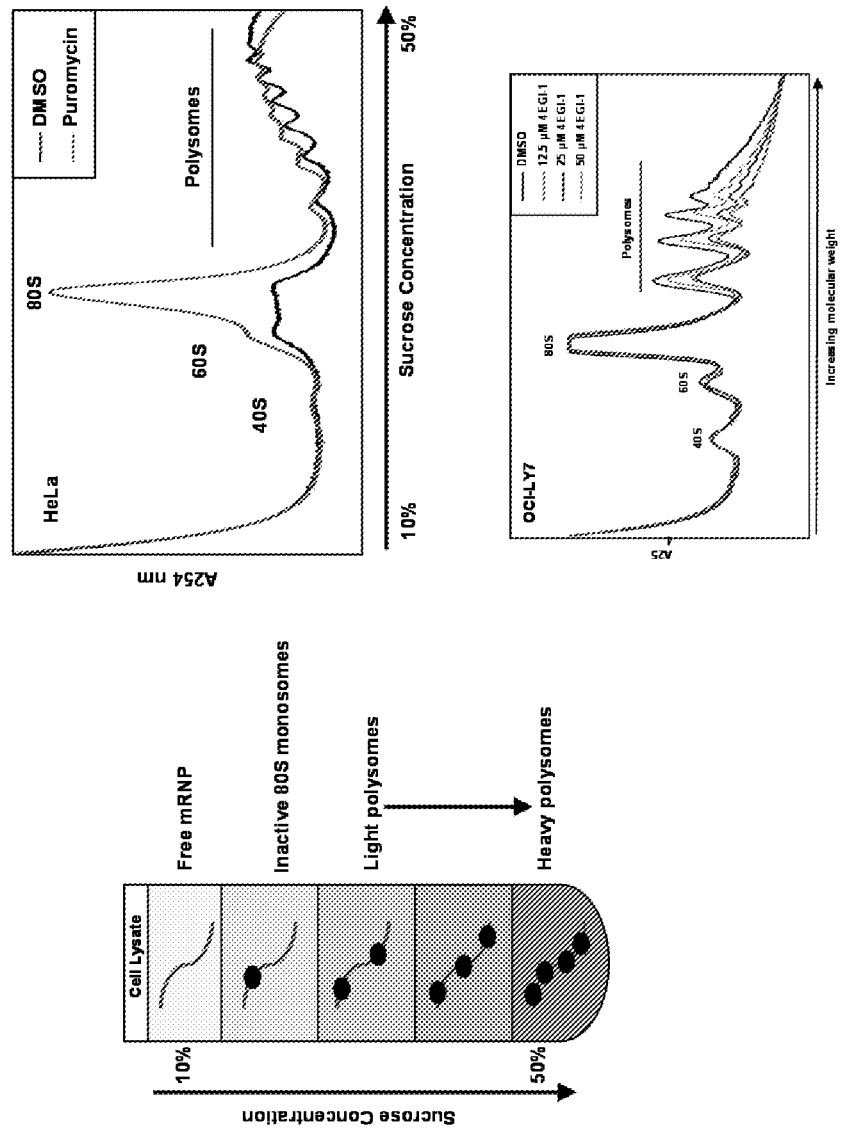
FIG. 11 shows a schematic drawing depicting the migration of polysomes through a sucrose gradient and date obtained (see EXAMPLE 5).

FIG. 11 shows results for puromycin and 4EGI-1, indicating a noticeable difference in polysome density. A decrease in "heavy" polysomes indicates decrease ribosome loading of mRNA for translation.

Example 6

Cell Proliferation Assay

Cells: AU565 (breast cancer $ER^-/PR^-$, $her2^-nue^+$)
1. Cells were resuspended in media containing 10% FBS and 2× gentamicin. Resuspended cells were transferred to an assay plate (100 μL aliquots; 5,200 cells/well).
2. test compound(s) were serially diluted in assay media. Aliquots of 100 μLof the test compound solution was added to the resuspended cells, creating a total volume of 200 μL.
3. Plates were incubated at 37 C for 91 hours.
4. 20 μL of Promega Substrate CellTiter 96 Aqueous One Solution Reagent was added to each well.
5. Plates were incubated at 37 C and read at 490 nm.

Figure 12:
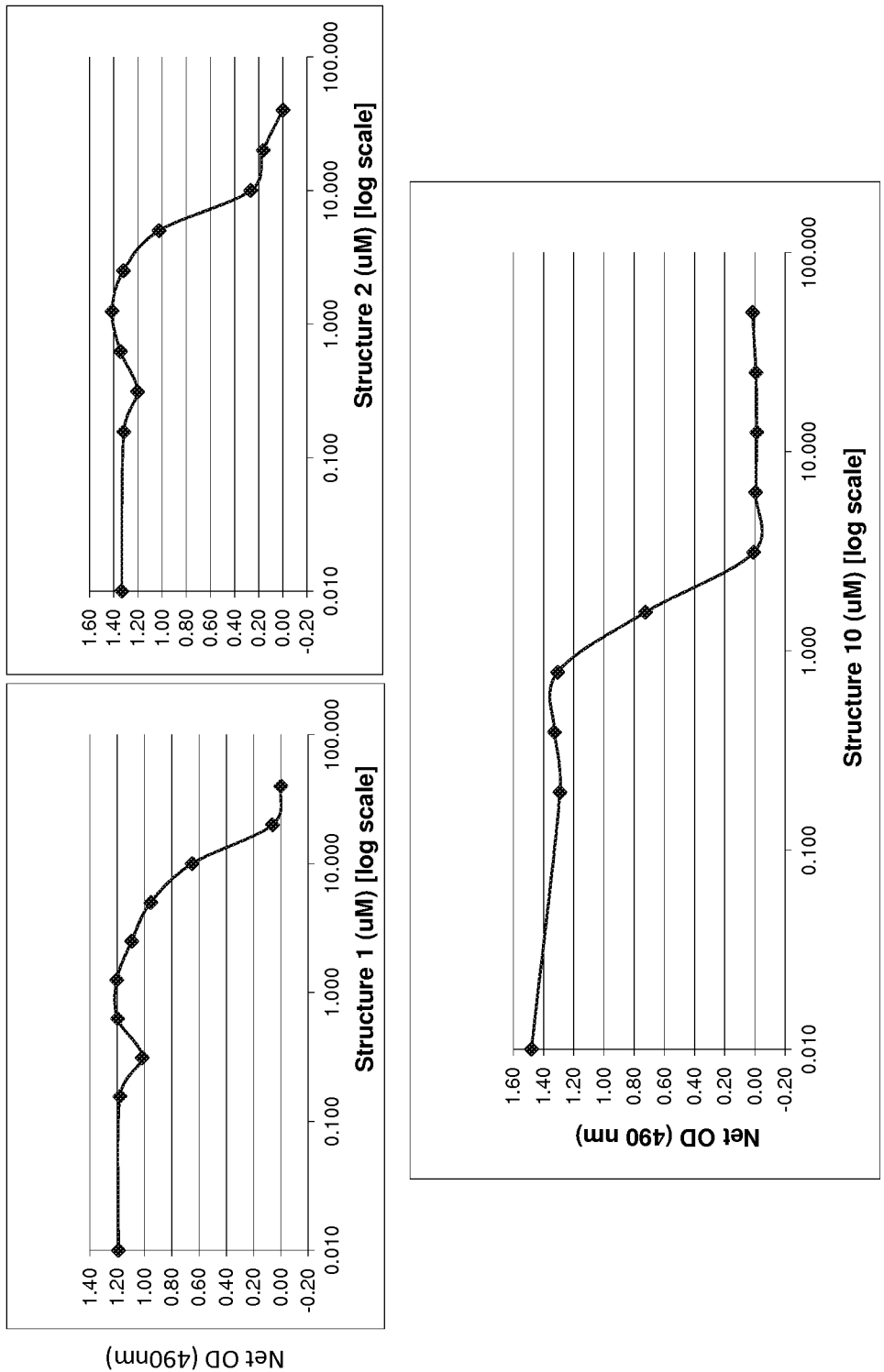
FIG. 12 is a series of plots showing data from cellular proliferation assays for Structure 1, Structure 2 and Structure 10 (see EXAMPLE 6).

Data are shown in Table VI below and in FIG. 12.

TABLE VI

| | Data: | | | | |
|---|---|---|---|---|---|
| | O.D. reading at 490 nm after 3 hours | | | | Relative cell growth |
| uM | Row G | Row H | Ave. | Net O.D. | (%) |
| 50.0 | 0.259 | 0.253 | 0.256 | 0.015 | 15 |
| 25.0 | 0.240 | 0.231 | 0.236 | −0.006 | 14 |
| 12.5 | 0.228 | 0.228 | 0.228 | −0.013 | 13 |
| 6.3 | 0.231 | 0.242 | 0.237 | −0.005 | 14 |
| 3.1 | 0.245 | 0.254 | 0.250 | 0.008 | 14 |
| 1.6 | 0.664 | 1.270 | 0.967 | 0.726 | 56 |
| 0.8 | 1.435 | 1.661 | 1.548 | 1.307 | 90 |
| 0.4 | 1.461 | 1.676 | 1.569 | 1.327 | 91 |
| 0.2 | 1.403 | 1.662 | 1.533 | 1.291 | 89 |
| 0.0 | 1.947 | 1.676 | 1.771 | 1.721 | 1.480 |
| 0.0 | 1.631 | 1.586 | 1.893 | | |
| 0.0 | 1.708 | 1.616 | | | |
| 0.0 | 1.681 | 1.704 | | | |
| Average Min OD (3.1-50.0 uM): | 0.241 | | | | |
| Max Net OD (0.0 uM): | 1.480 | | | | |
| Calculated O.D. for $ED_{50}$: | 0.740 | | | | |

TABLE VII

Summary of Anti-proliferative activity against AU-565

| | $ED_{50}$ (μM) | % Growth Inhibition/μM |
|---|---|---|
| 4EGI-1, Isomer E | 21-32 | 60/40 |
| 4EGI-1, Isomer Z | 4.8-7.1 | 30/10 |
| Structure 1 | 8.5-12.8 | 70/40 |
| Structure 2 | 5.6-8.4 | 79/40 |
| Structure 10 | 1.2-1.8 | 85/3.1 |

Example 7

Cap Affinity "Pull-Down" Assay

This assay measures displacement of eIF4E from eIF4G in vitro and in vivo.

Materials:
Cell or tumor lysates
Agarose conjugated m$^7$GTP (may also use GDP)
Free GDP
Free m$^7$GTP
Test compounds as 40 mM master solutions in DMSO
Antibodies and other detection reagents 1. Cells were treated with 25 μM, 50 μM or other desired concentrations of the test compound (the same volume DMSO as a control) for 8 hours.
2. Cells were harvested by scraping, collected by centrifugation, and lysed in cell lysis buffer.
3. Cell lysates were incubated with m$^7$GTP Sepharose beads (Pharmacia) for 1 hr at 4 C.
4. The resin was washed with lysis buffer.
5. Bound protein were eluted from the resin, thereby separating bound proteins from free m$^7$GTP.
6. The eluate was resolved using SDS-PAGE and analyzed by Western blotting using a polyclonal antibody against 4E-BP1 (Cell Signaling Technology) and monoclonal antibodies against eIF4E and eIF4G (Transduction Laboratories).
7. For the in vivo pull-down: tumor tissue obtained from mice was lysed and treated with the test compound or DMSO.

Figure 13:
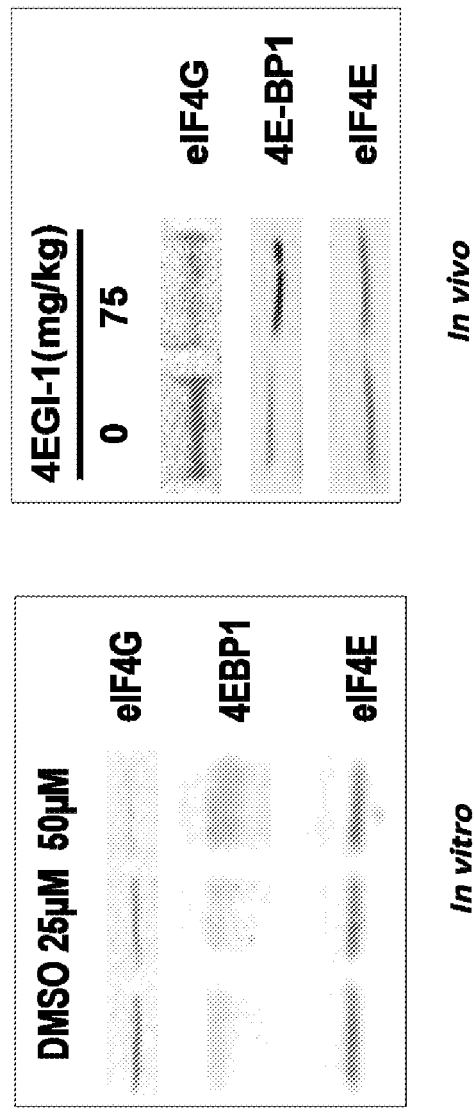
FIG. 13 shows Western blot analysis from pull down assays for known eIF4E inhibitor, 4EGI-1.
Figure 14:
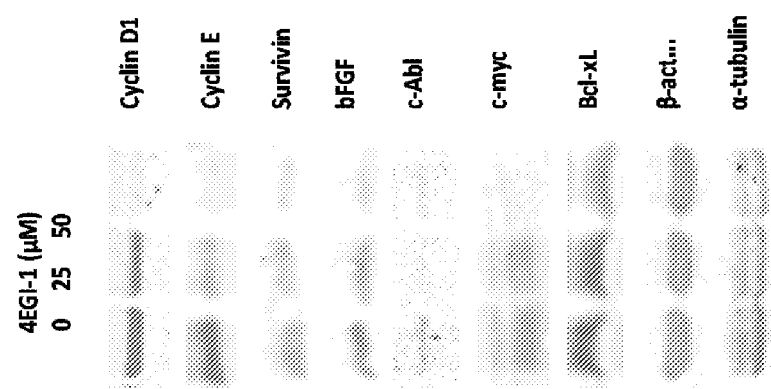
FIG. 14 expression of proteins in a xenograft model (see EXAMPLE 7). 4EGI-1 down-regulates translation of mRNA for growth-promoting and oncogenic proteins, while housekeeping proteins (e.g., actin and tubulin) are unaffected.
Figure 15:
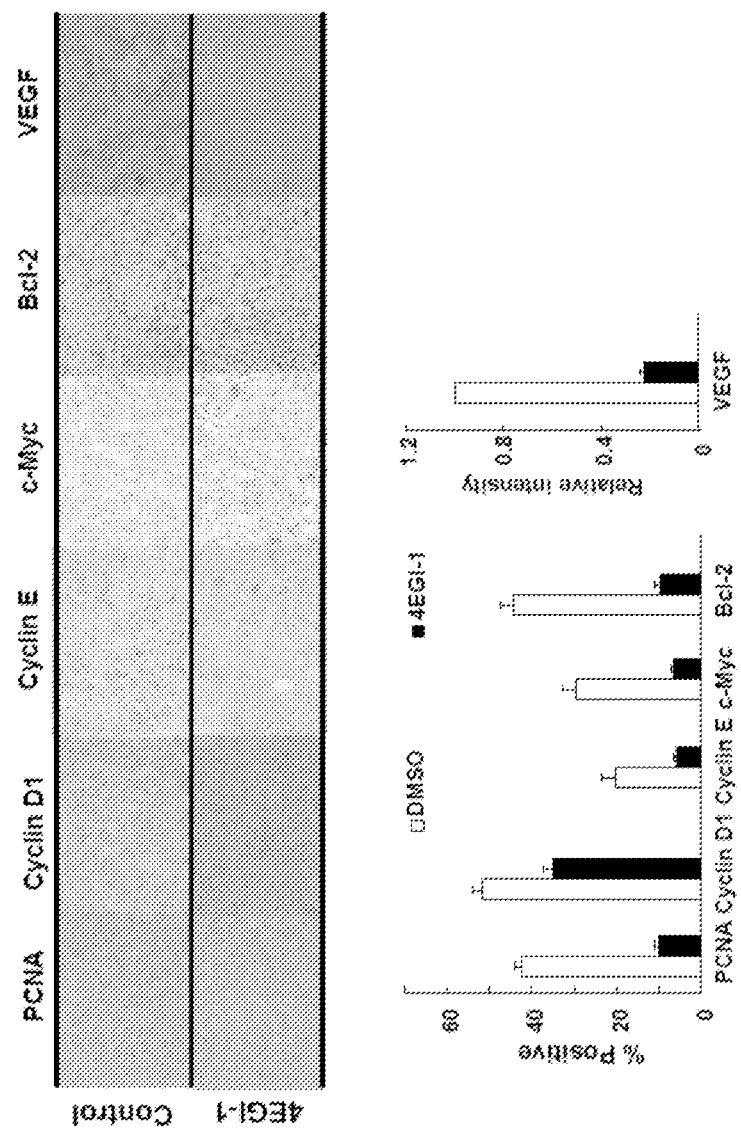
FIG. 15 are immunostaining and quantified data of protein expression from xenograft models (see EXAMPLE 7).

FIGS. 13 and 14 show results using various test compounds and cell lines or tissue samples.

Example 8

In Vivo Xenograft Studies of Tumor Growth Inhibition

Establishment and Treatment of CRL-1500 Human Breast Xenografts

Materials
CRL-1500 human Breast Cancer Cells
Anesthetic agents per regulations
Matrigel
Surgical equipment suitable for mouse surgery
Slow release estrogen pellet (60-90 days)

1. Human breast cancer cells were grown to obtain ≈5×10$^6$ cells for each tumor.
2. Cells were harvested and washed in PBS.
3. Harvested and washed cells were resuspended in 50% Matrigel™/medium at a density of ≈5 million cells in 25 μL (always kept on ice).
4. Female mice were anesthetized and immobilized.
5. Immobilized mice were inoculated with a slow release (60 days) Estrogen pellet into the sub-scapular region.
6. The mammary fat pad was exposed by incision, and 25 μL of the cell suspension was injected in 3 to 4th inguinal mammary fat pad.
7. The incision was closed by suture, and tumors were allowed to grow to measurable size (≈120-150 mm$^3$).
8. Mice with tumors of comparable size were selected and randomized into treatment and control groups. Mice were observed daily.
9. The mice were injected with a test compound or vehicle alone twice daily with at least 10 hrs time interval between doses.
10. Tumor dimensions were measured weekly with calipers (longest and shortest axes in mm).
11. Tumor volume was calculated from tumor dimensions following formula for volume of a prolate ellipsoid, as per NIH-protocols (L×W$^2$/2, where L is the longer and W the shorter of the two axes).
12. At the conclusion of the experiment, mice were sacrificed by $CO_2$ asphyxiation.
13. Tumors were dissected, removed and weighed.
14. The removed tumors were fixed in formalin solution or flash frozen and processed for histology/immunocytochemistry, or pull-down.

Establishment and Treatment of CRL-2813 Human Melanoma Xenografts

1. CRL-2813 cancer cells were grown to obtain ≈5×10$^6$ cells for each tumor.
2. Cells were harvested and washed in PBS.
3. Harvested and washed cells were resuspended in 50% Matrigel™/medium at a density of ≈5×10$^6$ cells in 100 μL.
4. 100 μL of the cell suspension was injected subcutaneously
5. Tumors were grown to ≈150 mm$^3$ (approx. 2 weeks).
1. Mice were randomly distributed to treatment and control groups and observed daily.
2. A test compound or vehicle alone was injected twice daily with at least 10 hrs time interval between doses
   Note: Vehicle: corn oil. Drug solution: 35 mg/mL of compound first dissolved in ethanol, mixed with corn oil followed by ethanol evaporation. Dosage: each dose=125 μL vehicle or drug suspension i.p.
3. Tumor volume was measured weekly.
4. At the conclusion of experiment, mice were sacrificed, and tumors were removed and weighed.
5. Remove tumor and weigh
6. The removed tumors were fixed in formalin solution or flash frozen and processed for histology/immunocytochemistry, or pull-down.

4EGI-1 inhibits expression of oncogenic proteins in melanoma tumors. CRL-2813 human melanoma xenografts were immunostained with antibodies specific for cyclin D1, cyclin E, c-myc, Bcl-2, VEGF or PCNA (FIG. 13). The bar graph is the quantification of immunostaining data (FIG. 14).

OTHER EMBODIMENTS

Other embodiments will be evident to those of skill in the art. It should be understood that the foregoing detailed description is provided for clarity only and is merely exemplary. The spirit and scope of the present disclosure are not limited to the above examples, but are encompassed by the following claims. The contents of all references cited herein are incorporated by reference in their entireties.

What is claimed is:

1. A compound of Formula I:

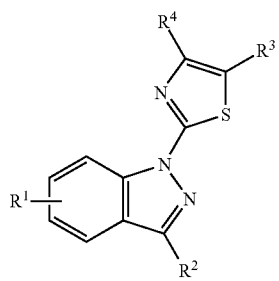

Formula I wherein, $R^1$ is selected from the group consisting of: an alkyl, haloalkyl, halide, Cl, $CF_3$, $CHF_2$, alkoxy, aryl, sulfone, sulfoxide, nitrile, carboxy, carboxamide, carbamate, urethane, amide, sulfamide, cyclic alkyl, amino and optionally substituted versions thereof;

$R^2$ is
  (a) selected from the group consisting of: a carboxy, hydroxy, amino, aminocarboxamide, aryl, heteroaryl, alkyl, alkylcarboxy, alkylcarboxamide and optionally substituted versions thereof, or
  (b) —C(O)—$R^{2'}$, wherein $R^{2'}$ is selected from the group consisting of: carboxy, hydroxy, amino, aminocarboxamide, aryl, heteroaryl, alkyl, alkylcarboxy, alkylcarboxamide,

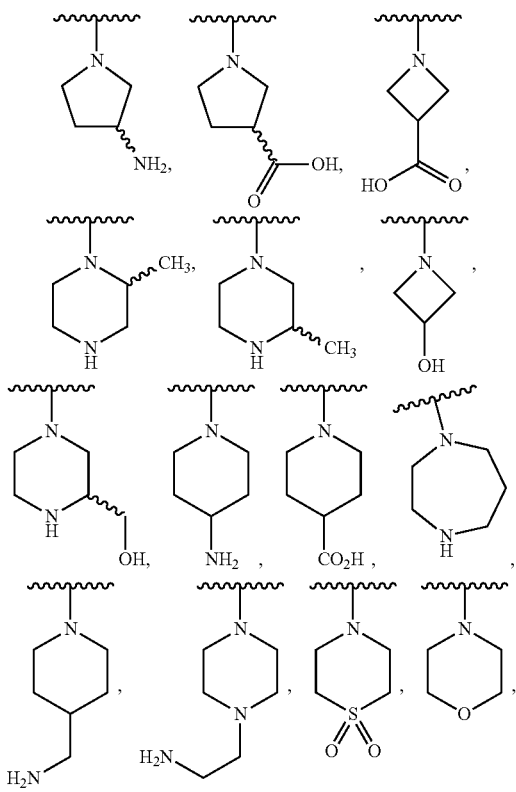

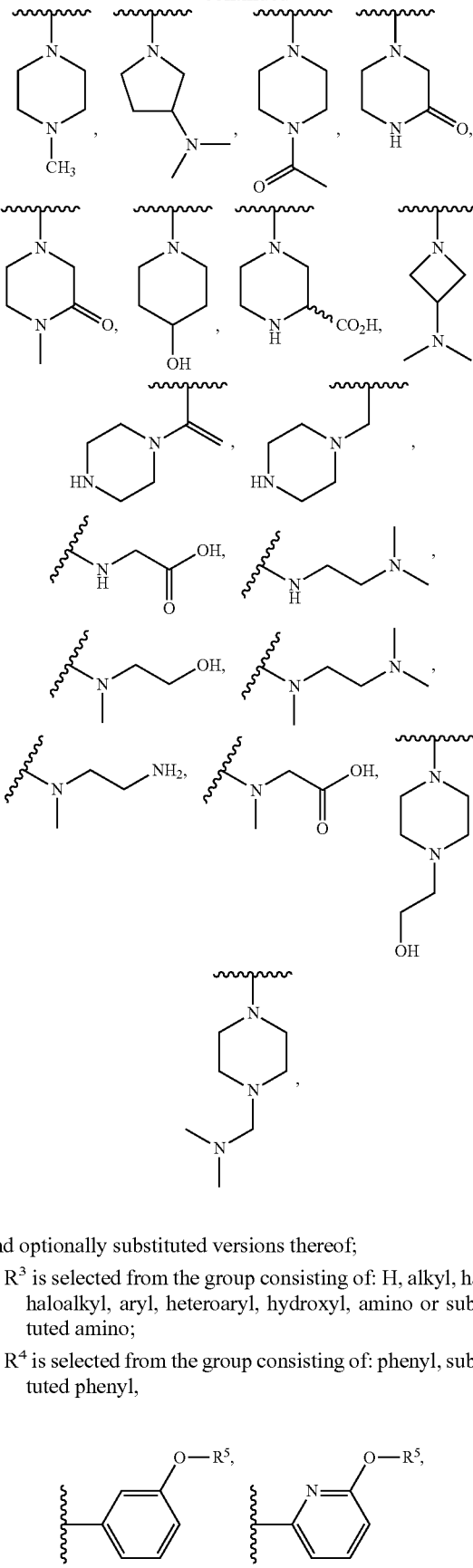

and optionally substituted versions thereof;

$R^3$ is selected from the group consisting of: H, alkyl, halo, haloalkyl, aryl, heteroaryl, hydroxyl, amino or substituted amino;

$R^4$ is selected from the group consisting of: phenyl, substituted phenyl,

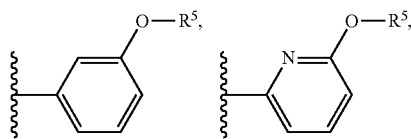

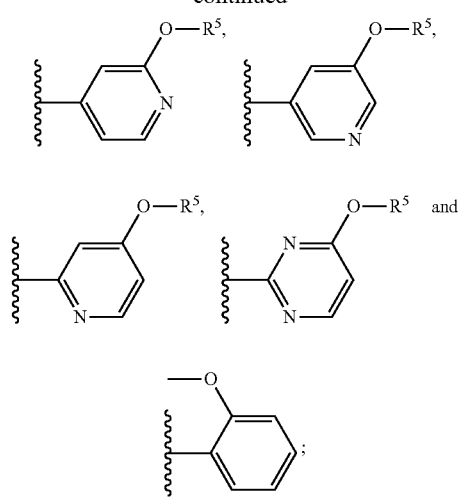
and
R⁵ is H or methyl.
2. The compound of claim 1, wherein R⁴ is
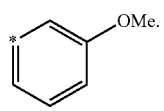
3. The compound of claim 1, wherein the compound is selected from
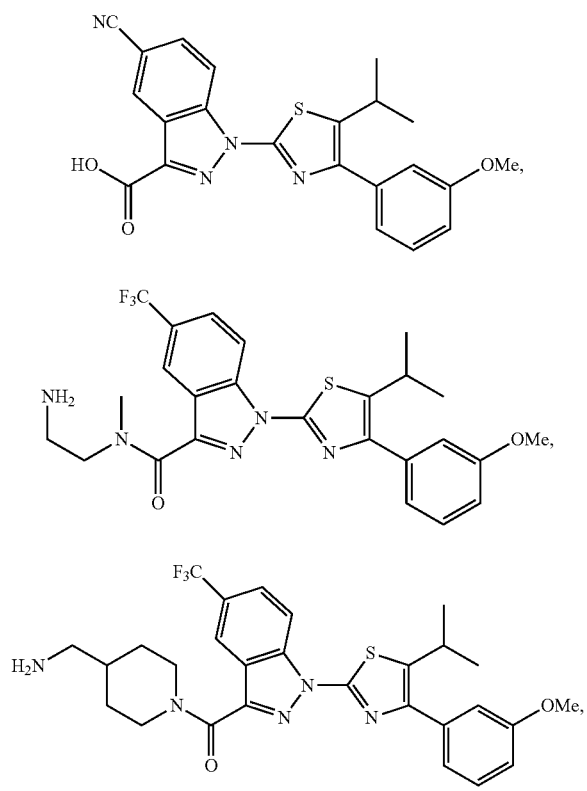
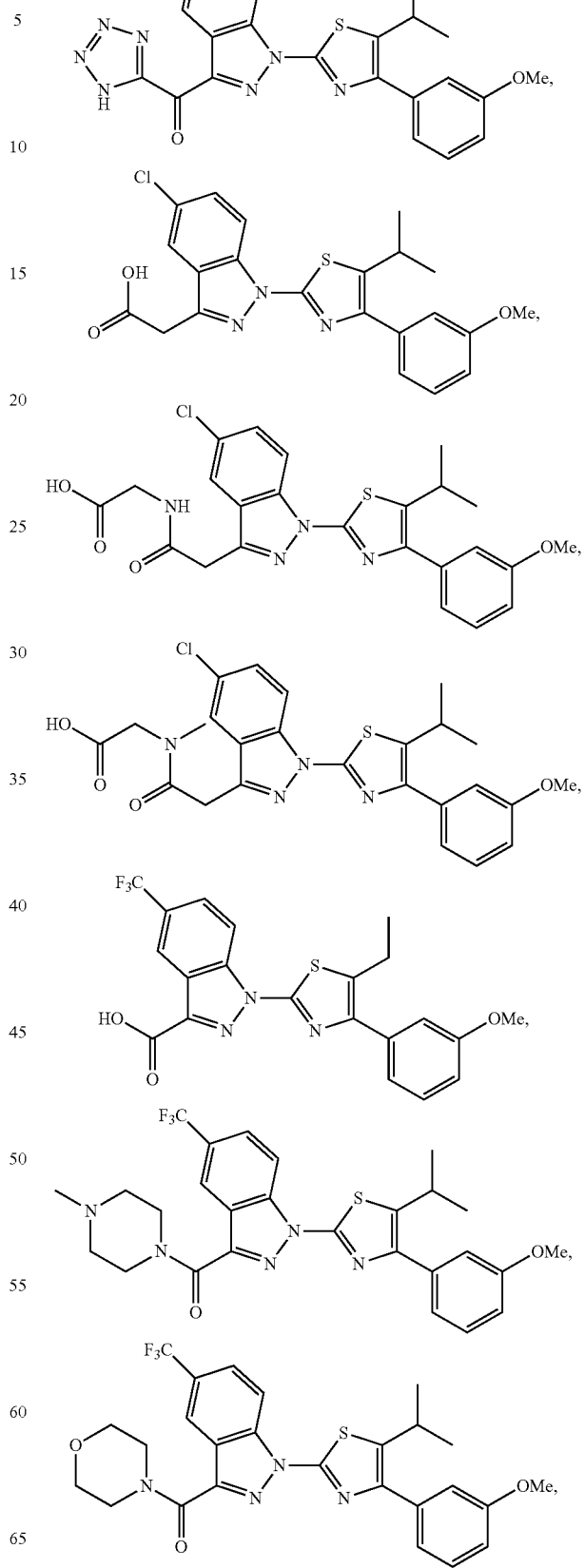

55
-continued
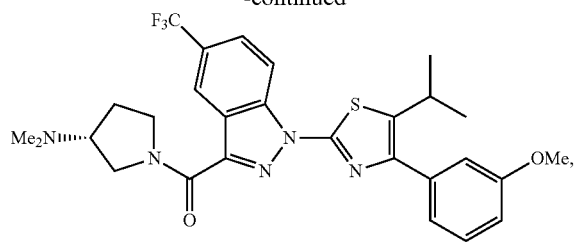
56
-continued
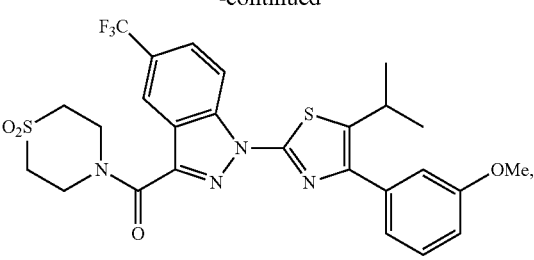
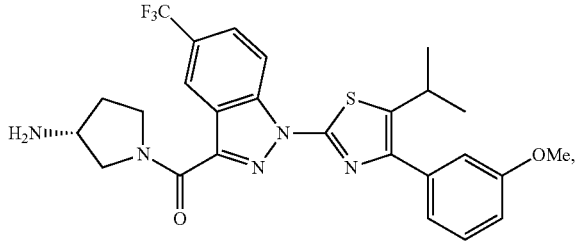
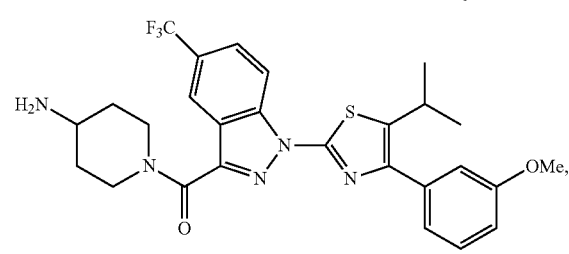
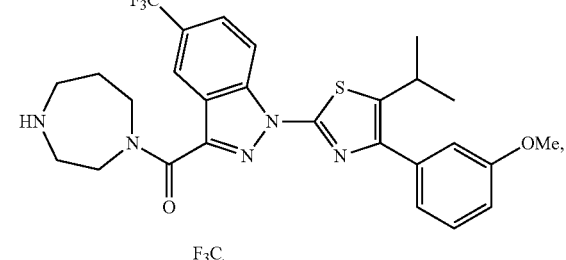
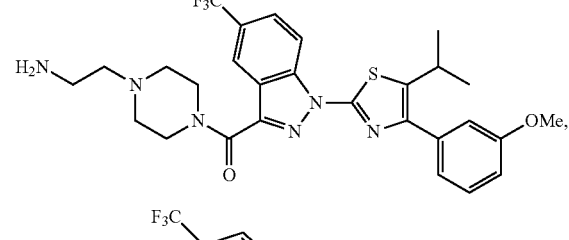
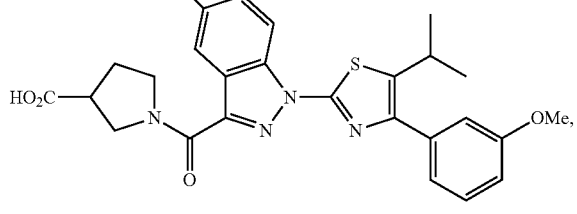
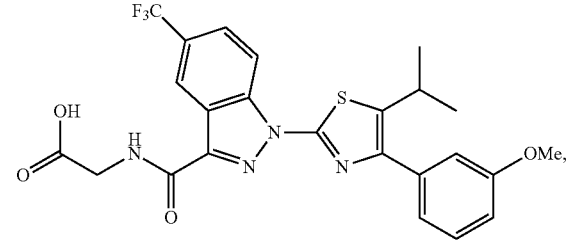

57
-continued
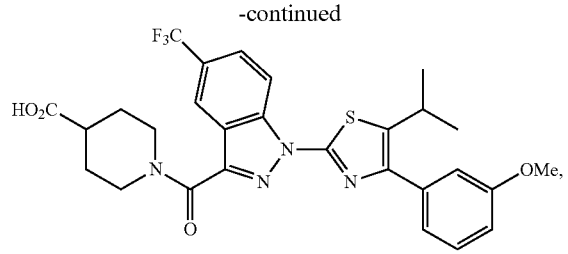
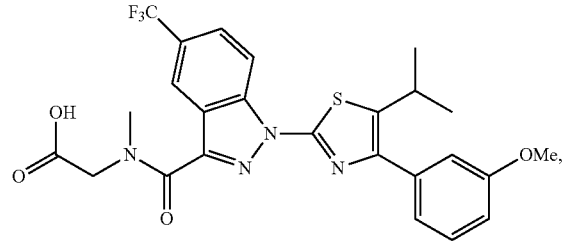
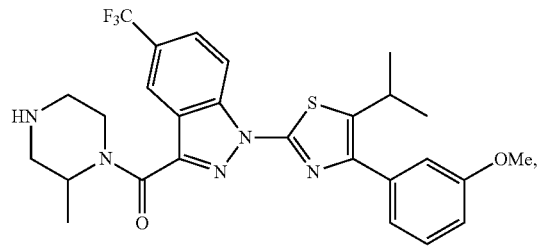
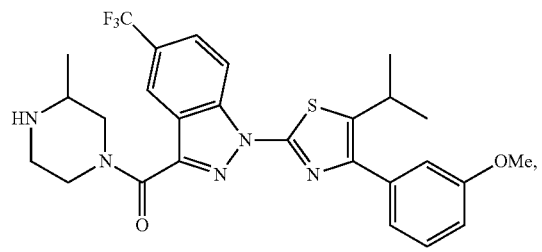
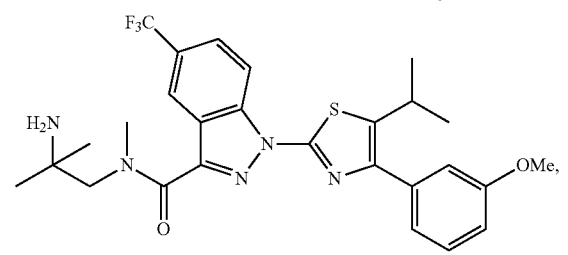
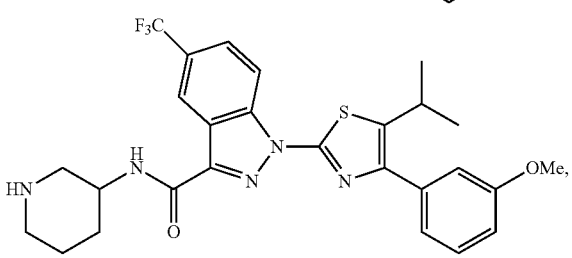
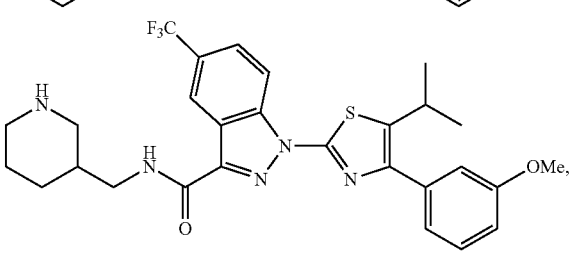
58
-continued
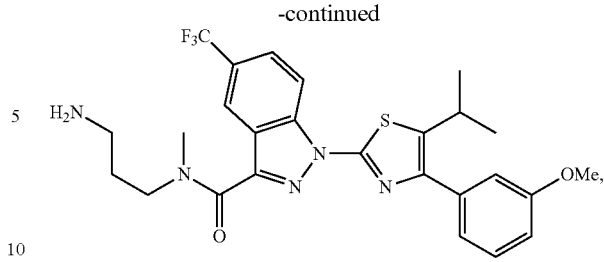
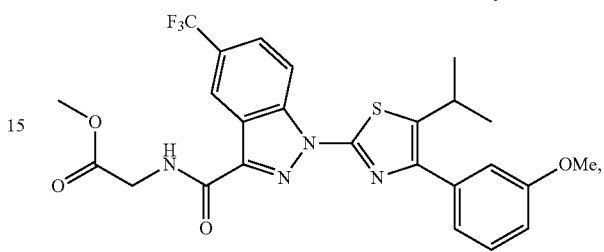
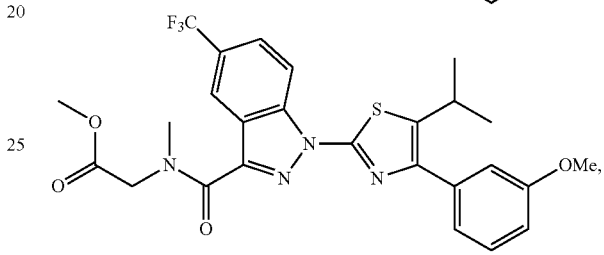
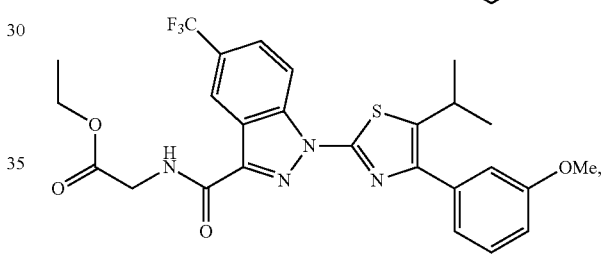
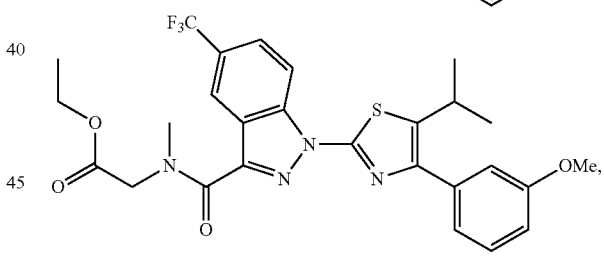
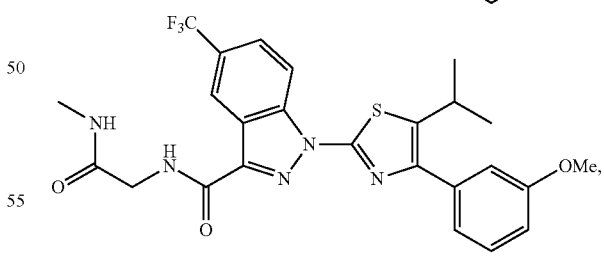
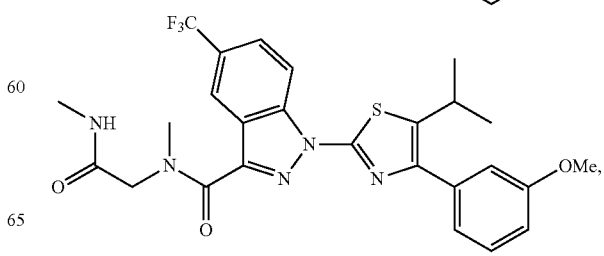

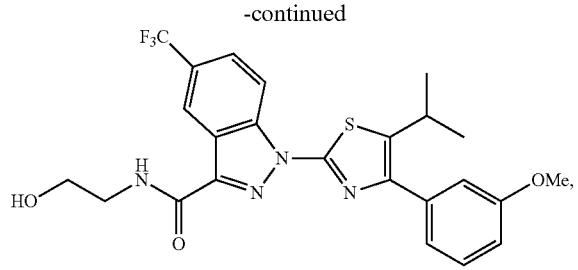
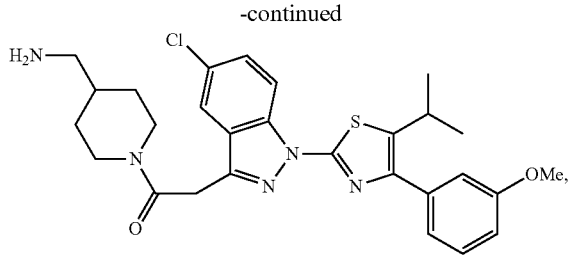
and

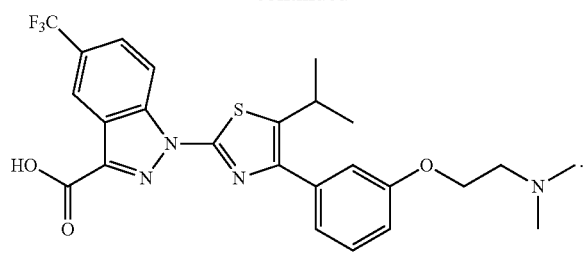
4. The compound of claim 1, wherein $R^3$ is H.
5. A compound of claim 1, wherein $R^2$ is —C(O)—$R^{2'}$, wherein $R^2$ is selected from the group consisting of: carboxy, hydroxy, amino, aminocarboxamide, aryl, heteroaryl, alkyl, alkylcarboxy, alkylcarboxamide,
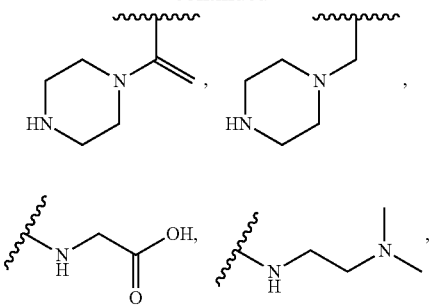
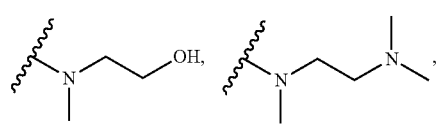
and optionally substituted versions thereof.
6. The compound of claim 5, wherein $R^4$ is
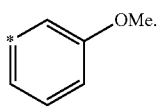
7. A compound of claim 1 of the formula:
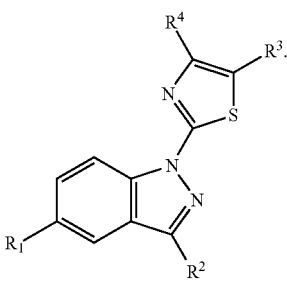

8. The compound of claim 7, wherein R⁴ is

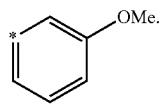

9. The compound of claim 7, wherein R¹ is selected from the group consisting of:
CN, CF₃ and Cl.

10. A compound of claim 5 of the formula:

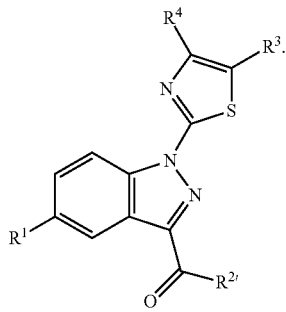

11. The compound of claim 10, wherein R⁴ is

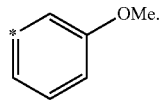

12. A method of reducing the proliferation of breast cancer in a subject in need thereof, the method comprising administering to the subject an effective amount of a compound of claim 1.

13. A compound of claim 1, wherein R² is selected from the group consisting of: a carboxy, hydroxy, amino, aminocarboxamide, aryl, heteroaryl, alkyl, alkylcarboxy, alkylcarboxamide and optionally substituted versions thereof.

14. A compound of claim 5, wherein R²' is selected from the group consisting of: a carboxy, hydroxy, amino, aminocarboxamide, aryl, heteroaryl, alkyl, alkylcarboxy, alkylcarboxamide and optionally substituted versions thereof.

15. A compound of claim 1, wherein R³ is alkyl.

16. A compound of claim 15, wherein R⁴ is

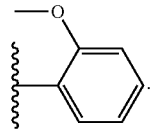

17. A compound of claim 16, wherein R³ is isopropyl.

18. A compound of claim 1, wherein R² is not unsubstituted alkyl.

19. A compound of the structural formula

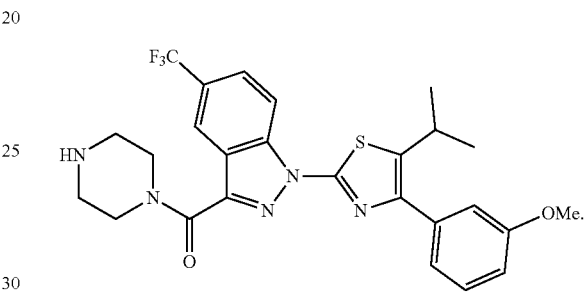

20. A method of reducing the proliferation of breast cancer in a subject in need thereof, the method comprising administering to the subject an effective amount of a compound of claim 19.

21. A compound of claim 1, wherein R¹ is selected from the group consisting of: an alkyl, haloalkyl, halide, Cl, CF₃, alkoxy, aryl, sulfone, sulfoxide, nitrile, carboxy, carboxamide, carbamate, urethane, amide, sulfamide, cyclic alkyl, amino and optionally substituted versions thereof.

22. A compound of claim 21, wherein R³ is H or alkyl.

* * * * *